United States Patent
Panicker et al.

(10) Patent No.: US 11,192,944 B2
(45) Date of Patent: Dec. 7, 2021

(54) METHODS OF INDUCING COMPLEMENT ACTIVITY

(71) Applicant: Bioverativ USA Inc., Waltham, MA (US)

(72) Inventors: Sandip Panicker, South San Francisco, CA (US); Stephen Moore, South San Francisco, CA (US); Pavel A. Nikitin, South San Francisco, CA (US); Tony Byun, South San Francisco, CA (US); Graham Parry, South San Francisco, CA (US)

(73) Assignee: Bioverativ USA Inc., Waltham, MA (US)

( * ) Notice: Subject to any disclaimer, the term of this patent is extended or adjusted under 35 U.S.C. 154(b) by 0 days.

(21) Appl. No.: 16/755,461

(22) PCT Filed: Oct. 11, 2018

(86) PCT No.: PCT/US2018/055444
§ 371 (c)(1),
(2) Date: Apr. 10, 2020

(87) PCT Pub. No.: WO2019/075220
PCT Pub. Date: Apr. 18, 2019

(65) Prior Publication Data
US 2020/0239556 A1    Jul. 30, 2020

Related U.S. Application Data

(60) Provisional application No. 62/637,135, filed on Mar. 1, 2018, provisional application No. 62/570,953, filed on Oct. 11, 2017.

(51) Int. Cl.
*C07K 16/18*    (2006.01)

(52) U.S. Cl.
CPC .......... *C07K 16/18* (2013.01); *C07K 2317/31* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 10,934,347 B2 | 3/2021 | Panicker et al. | |
| 2009/0214538 A1* | 8/2009 | Fung | A61P 27/00 424/135.1 |
| 2009/0280128 A1 | 11/2009 | Kamogawa et al. | |
| 2014/0286936 A1 | 9/2014 | Chambers et al. | |
| 2015/0239987 A1* | 8/2015 | Liang | C07K 16/18 424/139.1 |
| 2019/0153079 A1 | 5/2019 | Panicker et al. | |

FOREIGN PATENT DOCUMENTS

| | | |
|---|---|---|
| JP | 2015-514111 A | 5/2015 |
| WO | WO 2009/029669 A1 | 3/2009 |
| WO | WO 2009/082624 A2 | 7/2009 |
| WO | WO 2011/041391 A1 | 4/2011 |
| WO | WO 2013/126746 A2 | 8/2013 |
| WO | WO 2013/152020 A1 | 10/2013 |
| WO | WO 2014/044793 A2 | 3/2014 |
| WO | WO 2015/051159 A1 | 4/2015 |
| WO | WO 2015/130826 A1 | 9/2015 |
| WO | WO 2017/176651 A1 | 10/2017 |
| WO | WO 2019/075220 A1 | 4/2019 |

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
Koenig "Mutational landscape of antibody variable domains reveals a switch modulating the interdomain conformational dynamics and antigen binding" PNAS E486-E495 (Year: 2017).*
Thurman "Complement Therapeutics in Autoimmune Disease" Front Immun 10(672): 1-9 (Year: 2019).*
Pio "The Role of Complement in Tumor Growth" Adv Exp Med Biol. 2014 ; 772: 229-262 (Year: 2014).*
Extended European Search Report dated Dec. 17, 2019 in connection with Application No. EP 17779607.5.
Invitation to Pay Additional Fees for Application No. PCT/US2017/025784 dated Jul. 11, 2017.
International Search Report and Written Opinion for Application No. PCT/US2017/025784 dated Sep. 7, 2017.
International Preliminary Report on Patentability for Application No. PCT/US2017/025784 dated Oct. 18, 2018.

* cited by examiner

*Primary Examiner* — Adam Weidner
(74) *Attorney, Agent, or Firm* — Wolf, Greenfield & Sacks, P.C.

(57) ABSTRACT

The present disclosure provides methods of inducing a complement activity on a surface of a cell comprising contacting the cell with an effective amount of an anti-Factor B antibody, wherein the anti-Factor B antibody inhibits dissociation of a C3bBb complex into a Factor Bb and a C3b.

13 Claims, 5 Drawing Sheets
Specification includes a Sequence Listing.

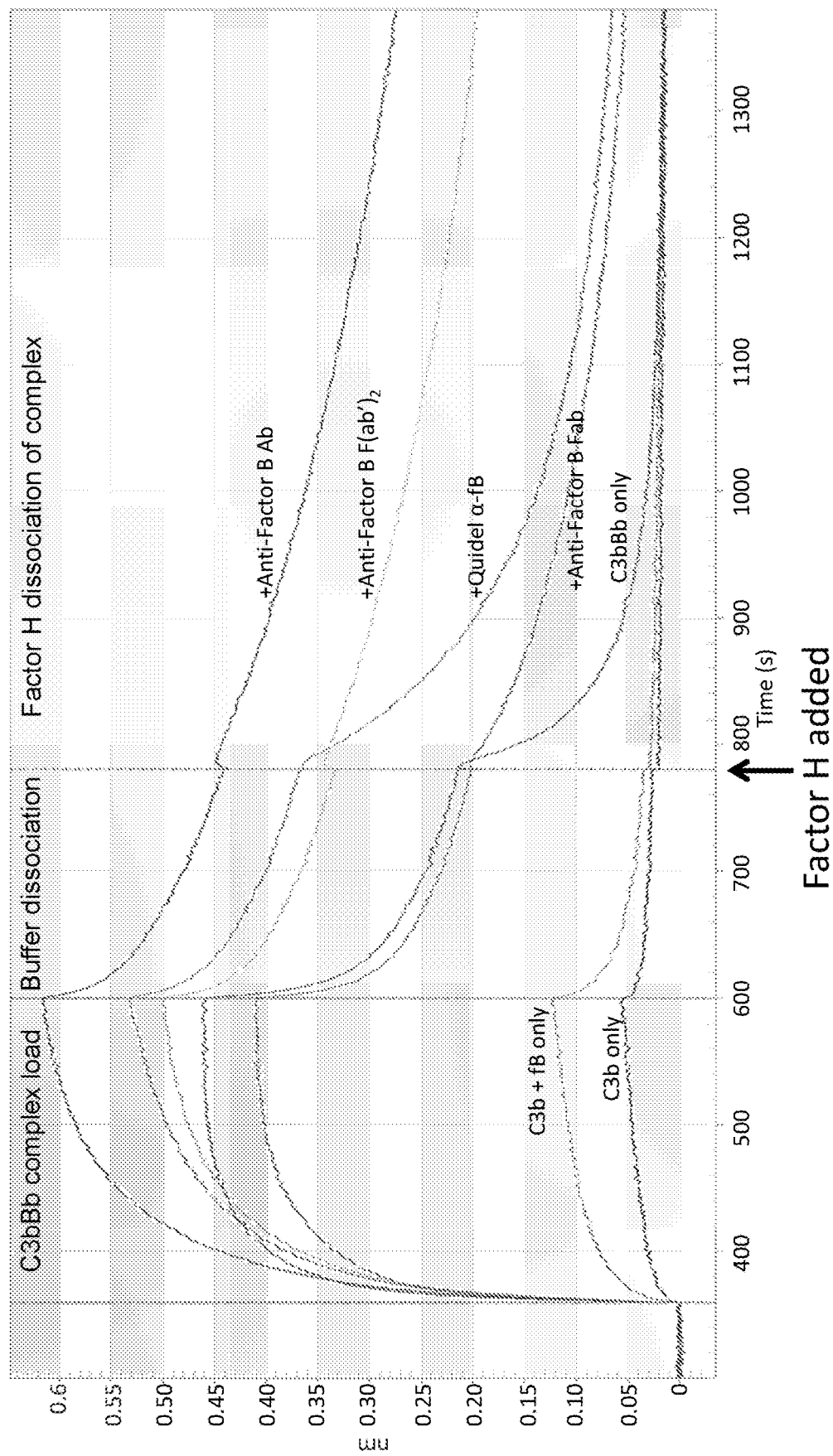

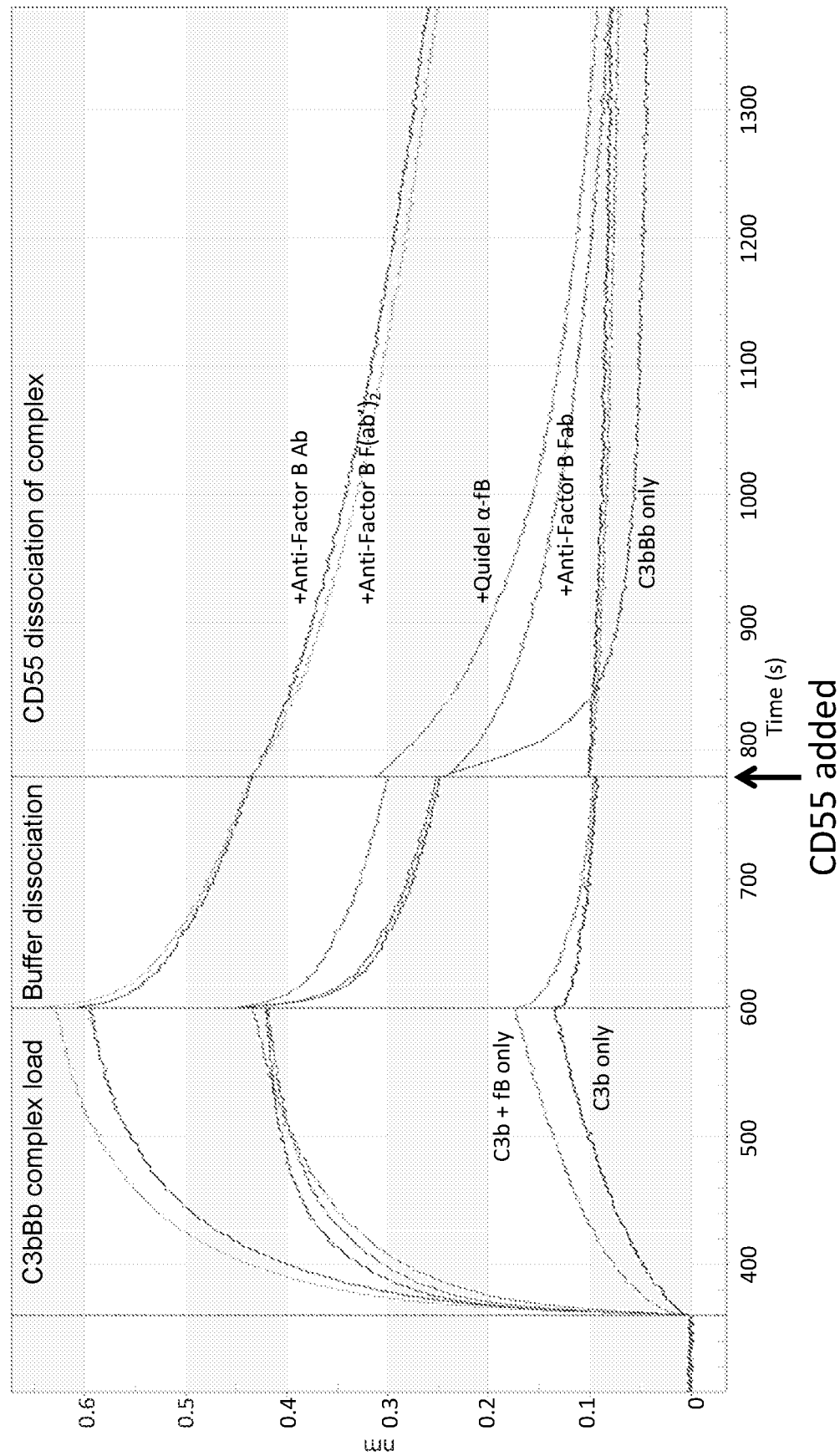

SEQUENCE LISTING

```
<160> NUMBER OF SEQ ID NOS: 15

<210> SEQ ID NO 1
<211> LENGTH: 8
<212> TYPE: PRT
<213> ORGANISM: Artificial Sequence
<220> FEATURE:
```

<223> OTHER INFORMATION: VH CDR1

<400> SEQUENCE: 1

Gly Tyr Ser Phe Thr Asp Tyr Leu
1               5

<210> SEQ ID NO 2
<211> LENGTH: 8
<212> TYPE: PRT
<213> ORGANISM: Artificial Sequence
<220> FEATURE:
<223> OTHER INFORMATION: VH CDR2

<400> SEQUENCE: 2

Ile Asn Pro Tyr Asn Gly Asp Ala
1               5

<210> SEQ ID NO 3
<211> LENGTH: 11
<212> TYPE: PRT
<213> ORGANISM: Artificial Sequence
<220> FEATURE:
<223> OTHER INFORMATION: VH CDR3

<400> SEQUENCE: 3

Ala Arg Leu Glu Asn Asp Tyr Gly Phe Thr Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: VL CDR1

<400> SEQUENCE: 4

Lys Ser Leu Leu His Ser Asn Gly Ile Thr Tyr
1               5                   10

<210> SEQ ID NO 5
<211> LENGTH: 3
<212> TYPE: PRT
<213> ORGANISM: Artificial Sequence
<220> FEATURE:
<223> OTHER INFORMATION: VL CDR2

<400> SEQUENCE: 5

Arg Met Ser
1

<210> SEQ ID NO 6
<211> LENGTH: 9
<212> TYPE: PRT
<213> ORGANISM: Artificial Sequence
<220> FEATURE:
<223> OTHER INFORMATION: VL CDR3

<400> SEQUENCE: 6

Ala Gln Met Leu Glu Arg Pro Trp Thr
1               5

<210> SEQ ID NO 7
<211> LENGTH: 118
<212> TYPE: PRT
<213> ORGANISM: Artificial Sequence
<220> FEATURE:
<223> OTHER INFORMATION: Anti-Factor B VH

```
<400> SEQUENCE: 7

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ser Phe Thr Asp Tyr
            20                  25                  30

Leu Met Asn Trp Val Lys Gln Ser His Gly Lys Ser Leu Glu Trp Ile
        35                  40                  45

Gly Arg Ile Asn Pro Tyr Asn Gly Asp Ala Phe Tyr Asn Gln Arg Phe
    50                  55                  60

Lys Gly Lys Ala Thr Leu Thr Val Asp Lys Ser Ser Thr Ala His
65                  70                  75                  80

Met Glu Leu Arg Ser Leu Thr Ser Glu Asp Ser Ala Leu Tyr Tyr Cys
                85                  90                  95

Ala Arg Leu Glu Asn Asp Tyr Gly Phe Thr Tyr Trp Gly Gln Gly Thr
            100                 105                 110

Leu Val Thr Val Ser Ala
            115

<210> SEQ ID NO 8
<211> LENGTH: 112
<212> TYPE: PRT
<213> ORGANISM: Artificial Sequence
<220> FEATURE:
<223> OTHER INFORMATION: Anti-Factor B VL

<400> SEQUENCE: 8

Asp Ile Val Met Thr Gln Ala Ala Phe Ser Asn Pro Val Thr Leu Gly
1               5                   10                  15

Thr Ser Ala Ser Ile Ser Cys Ser Ser Ser Lys Ser Leu Leu His Ser
            20                  25                  30

Asn Gly Ile Thr Tyr Leu Tyr Trp Tyr Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Met
                85                  90                  95

Leu Glu Arg Pro Trp Thr Phe Gly Gly Gly Thr Lys Leu Glu Ile Lys
            100                 105                 110

<210> SEQ ID NO 9
<211> LENGTH: 444
<212> TYPE: PRT
<213> ORGANISM: Artificial Sequence
<220> FEATURE:
<223> OTHER INFORMATION: Anti-Factor B Heavy Chain

<400> SEQUENCE: 9

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ser Phe Thr Asp Tyr
            20                  25                  30

Leu Met Asn Trp Val Lys Gln Ser His Gly Lys Ser Leu Glu Trp Ile
        35                  40                  45

Gly Arg Ile Asn Pro Tyr Asn Gly Asp Ala Phe Tyr Asn Gln Arg Phe
    50                  55                  60
```

```
Lys Gly Lys Ala Thr Leu Thr Val Asp Lys Ser Ser Thr Ala His
 65                  70                  75                  80

Met Glu Leu Arg Ser Leu Thr Ser Glu Asp Ser Ala Leu Tyr Tyr Cys
                 85                  90                  95

Ala Arg Leu Glu Asn Asp Tyr Gly Phe Thr Tyr Trp Gly Gln Gly Thr
            100                 105                 110

Leu Val Thr Val Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
210                 215                 220

Pro Cys Pro Ala Pro Glu Phe Glu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
        355                 360                 365

Phe Tyr Pro Ser Asp Ile Ala Val Glu Trp Glu Ser Asn Gly Gln Pro
        370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 10
<211> LENGTH: 216
<212> TYPE: PRT
<213> ORGANISM: Artificial Sequence
<220> FEATURE:
```

<223> OTHER INFORMATION: Antifactor B Light Chain

<400> SEQUENCE: 10

```
Asp Ile Val Met Thr Gln Ala Ala Phe Ser Asn Pro Val Thr Leu Gly
1               5                   10                  15

Thr Ser Ala Ser Ile Ser Cys Ser Ser Lys Ser Leu Leu His Ser
            20                  25                  30

Asn Gly Ile Thr Tyr Leu Tyr Trp Tyr Leu Gln Arg Pro Gly Gln Ser
        35                  40                  45

Pro Gln Leu Leu Ile Tyr Arg Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Met
                85                  90                  95

Leu Glu Arg Pro Trp Thr Phe Gly Gly Gly Thr Lys Leu Glu Ile Lys
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly
    210                 215
```

<210> SEQ ID NO 11
<211> LENGTH: 354
<212> TYPE: DNA
<213> ORGANISM: Artificial Sequence
<220> FEATURE:
<223> OTHER INFORMATION: Anti-Factor B VH

<400> SEQUENCE: 11

```
gaagtgcaac tccaacagag cggaccagaa cttgtgaagc ccggagcctc agtgaagatg      60
tcctgtaagg cttccggata ttccttcact gattacctga tgaactgggt caagcagagc     120
catggaaagt ccctggagtg gattgggcgc atcaatccgt acaacggcga tgcgttctac     180
aaccagcggt ttaaggggaa ggccaccctg accgtggaca gtcatcgtc caccgcccac      240
atggagttga gatccctgac ctcggaggac agcgccctct actactgcgc aaggctggaa     300
aacgattacg gcttcaccta ctggggccag ggtactctgg tcactgtgtc cgct            354
```

<210> SEQ ID NO 12
<211> LENGTH: 1335
<212> TYPE: DNA
<213> ORGANISM: Artificial Sequence
<220> FEATURE:
<223> OTHER INFORMATION: Anti-factor B Heavy chain

<400> SEQUENCE: 12

```
gaagtgcaac tccaacagag cggaccagaa cttgtgaagc ccggagcctc agtgaagatg      60
```

```
tcctgtaagg cttccggata ttccttcact gattacctga tgaactgggt caagcagagc      120
catggaaagt ccctggagtg gattgggcgc atcaatccgt acaacggcga tgcgttctac      180
aaccagcggt ttaaggggaa ggccaccctg accgtggaca gtcatcgtc caccgcccac       240 atggagttga gatccctgac ctcggaggac agcgccctct actactgcgc aaggctggaa      300
aacgattacg gcttcaccta ctggggccag gtactctgg tcactgtgtc cgcttccacc       360
aagggcccat ccgtcttccc cctggcgccc tgctccagga gcacctccga gagcacagcc      420
gccctgggct gcctggtcaa ggactacttc cccgaaccgg tgacggtgtc gtggaactca      480
ggcgccctga ccagcggcgt gcacaccttc ccggctgtcc tacagtcctc aggactctac      540
tccctcagca gcgtggtgac cgtgccctcc agcagcttgg gcacgaagac ctacacctgc      600
aatgtagatc acaagcccag caacaccaag gtggacaaga gagttgagtc caaatatggt      660 ccccatgcc caccatgccc agcacctgag ttcgaggggg gaccatcagt cttcctgttc       720
cccccaaaac ccaaggacac tctcatgatc tcccggaccc ctgaggtcac gtgcgtggtg      780
gtggacgtga gccaggaaga ccccgaggtc cagttcaact ggtacgtgga tggcgtggag      840
gtgcataatg ccaagacaaa gccgcgggag gagcagttca acagcacgta ccgtgtggtc      900
agcgtcctca ccgtcctgca ccaggactgg ctgaacggca aggagtacaa gtgcaaggtc      960
tccaacaaag gcctcccgtc ctccatcgag aaaaccatct ccaaagccaa agggcagccc      1020
cgagagccac aggtgtacac cctgcccca tcccaggagg agatgaccaa gaaccaggtc      1080
agcctgacct gcctggtcaa aggcttctac cccagcgaca tcgccgtgga gtgggagagc      1140
aatgggcagc cggagaacaa ctacaagacc acgcctcccg tgctggactc cgacggctcc      1200
ttcttcctct acagcaggct aaccgtggac aagagcaggt ggcaggaggg gaatgtcttc      1260
tcatgctccg tgatgcatga ggctctgcac aaccactaca cacagaagag cctctccctg      1320
tctctgggta aatga                                                       1335

<210> SEQ ID NO 13
<211> LENGTH: 339
<212> TYPE: DNA
<213> ORGANISM: Artificial Sequence
<220> FEATURE:
<223> OTHER INFORMATION: VL

<400> SEQUENCE: 13
gatatcgtga tgacccaggc tgccttctcc aaccctgtga ctctcggaac ctccgcctca      60
atctcctgct cgtcatccaa gtccctgctt cactcgaacg ggattaccta cctgtattgg      120
tacttgcaaa gaccgggcca gagccccag ctgctgatct accgcatgtc gaacctggcc       180
agcggagtgc cagaccggtt ctccggttct ggttccggga ctgacttcac tctgcggatt      240
agcagggtgg aagcagagga cgtcggagtg tactactgtg cgcagatgct cgagcgcccg      300
tggacctttg gcggaggcac caagctggaa atcaagact                             339

<210> SEQ ID NO 14
<211> LENGTH: 657
<212> TYPE: DNA
<213> ORGANISM: Artificial Sequence
<220> FEATURE:
<223> OTHER INFORMATION: Light Chain

<400> SEQUENCE: 14
gatatcgtga tgacccaggc tgccttctcc aaccctgtga ctctcggaac ctccgcctca      60
```

-continued

| | |
|---|---|
| atctcctgct cgtcatccaa gtccctgctt cactcgaacg ggattaccta cctgtattgg | 120 |
| tacttgcaaa gaccgggcca gagccccag ctgctgatct accgcatgtc gaacctggcc | 180 |
| agcggagtgc cagaccggtt ctccggttct ggttccggga ctgacttcac tctgcggatt | 240 |
| agcagggtgg aagcagagga cgtcggagtg tactactgtg cgcagatgct cgagcgcccg | 300 |
| tggacctttg gcggaggcac caagctggaa atcaagactg tggctgcacc atctgtcttc | 360 |
| atcttcccgc catctgatga gcagttgaaa tctggaactg cctctgttgt gtgcctgctg | 420 |
| aataacttct atcccagaga ggccaaagta cagtggaagg tggataacgc cctccaatcg | 480 |
| ggtaactccc aggagagtgt cacagagcag gacagcaagg acagcaccta cagcctcagc | 540 |
| agcaccctga cgctgagcaa agcagactac gagaaacaca aagtctacgc ctgcgaagtc | 600 |
| acccatcagg gcctgagctc gcccgtcaca aagagcttca caggggaga gtgttag | 657 |

<210> SEQ ID NO 15
<211> LENGTH: 764
<212> TYPE: PRT
<213> ORGANISM: Artificial Sequence
<220> FEATURE:
<223> OTHER INFORMATION: human Factor Bb

<400> SEQUENCE: 15

Met Gly Ser Asn Leu Ser Pro Gln Leu Cys Leu Met Pro Phe Ile Leu
1               5                   10                  15

Gly Leu Leu Ser Gly Gly Val Thr Thr Thr Pro Trp Ser Leu Ala Arg
                20                  25                  30

Pro Gln Gly Ser Cys Ser Leu Glu Gly Val Glu Ile Lys Gly Gly Ser
            35                  40                  45

Phe Arg Leu Leu Gln Glu Gly Gln Ala Leu Glu Tyr Val Cys Pro Ser
        50                  55                  60

Gly Phe Tyr Pro Tyr Pro Val Gln Thr Arg Thr Cys Arg Ser Thr Gly
65                  70                  75                  80

Ser Trp Ser Thr Leu Lys Thr Gln Asp Gln Lys Thr Val Arg Lys Ala
                85                  90                  95

Glu Cys Arg Ala Ile His Cys Pro Arg Pro His Asp Phe Glu Asn Gly
            100                 105                 110

Glu Tyr Trp Pro Arg Ser Pro Tyr Tyr Asn Val Ser Asp Glu Ile Ser
        115                 120                 125

Phe His Cys Tyr Asp Gly Tyr Thr Leu Arg Gly Ser Ala Asn Arg Thr
130                 135                 140

Cys Gln Val Asn Gly Arg Trp Ser Gly Gln Thr Ala Ile Cys Asp Asn
145                 150                 155                 160

Gly Ala Gly Tyr Cys Ser Asn Pro Gly Ile Pro Ile Gly Thr Arg Lys
                165                 170                 175

Val Gly Ser Gln Tyr Arg Leu Glu Asp Ser Val Thr Tyr His Cys Ser
            180                 185                 190

Arg Gly Leu Thr Leu Arg Gly Ser Gln Arg Arg Thr Cys Gln Glu Gly
        195                 200                 205

Gly Ser Trp Ser Gly Thr Glu Pro Ser Cys Gln Asp Ser Phe Met Tyr
    210                 215                 220

Asp Thr Pro Gln Glu Val Ala Glu Ala Phe Leu Ser Ser Leu Thr Glu
225                 230                 235                 240

Thr Ile Glu Gly Val Asp Ala Glu Asp Gly His Gly Pro Gly Glu Gln
                245                 250                 255

Gln Lys Arg Lys Ile Val Leu Asp Pro Ser Gly Ser Met Asn Ile Tyr

```
                260                 265                 270
Leu Val Leu Asp Gly Ser Asp Ser Ile Gly Ala Ser Asn Phe Thr Gly
            275                 280                 285

Ala Lys Lys Cys Leu Val Asn Leu Ile Glu Lys Val Ala Ser Tyr Gly
        290                 295                 300

Val Lys Pro Arg Tyr Gly Leu Val Thr Tyr Ala Thr Tyr Pro Lys Ile
305                 310                 315                 320

Trp Val Lys Val Ser Glu Ala Asp Ser Ser Asn Ala Asp Trp Val Thr
                325                 330                 335

Lys Gln Leu Asn Glu Ile Asn Tyr Glu Asp His Lys Leu Lys Ser Gly
            340                 345                 350

Thr Asn Thr Lys Lys Ala Leu Gln Ala Val Tyr Ser Met Met Ser Trp
        355                 360                 365

Pro Asp Asp Val Pro Pro Glu Gly Trp Asn Arg Thr Arg His Val Ile
        370                 375                 380

Ile Leu Met Thr Asp Gly Leu His Asn Met Gly Gly Asp Pro Ile Thr
385                 390                 395                 400

Val Ile Asp Glu Ile Arg Asp Leu Leu Tyr Ile Gly Lys Asp Arg Lys
                405                 410                 415

Asn Pro Arg Glu Asp Tyr Leu Asp Val Tyr Val Phe Gly Val Gly Pro
            420                 425                 430

Leu Val Asn Gln Val Asn Ile Asn Ala Leu Ala Ser Lys Lys Asp Asn
        435                 440                 445

Glu Gln His Val Phe Lys Val Lys Asp Met Glu Asn Leu Glu Asp Val
        450                 455                 460

Phe Tyr Gln Met Ile Asp Glu Ser Gln Ser Leu Ser Leu Cys Gly Met
465                 470                 475                 480

Val Trp Glu His Arg Lys Gly Thr Asp Tyr His Lys Gln Pro Trp Gln
                485                 490                 495

Ala Lys Ile Ser Val Ile Arg Pro Ser Lys Gly His Glu Ser Cys Met
            500                 505                 510

Gly Ala Val Val Ser Glu Tyr Phe Val Leu Thr Ala Ala His Cys Phe
        515                 520                 525

Thr Val Asp Asp Lys Glu His Ser Ile Lys Val Ser Val Gly Gly Glu
        530                 535                 540

Lys Arg Asp Leu Glu Ile Glu Val Val Leu Phe His Pro Asn Tyr Asn
545                 550                 555                 560

Ile Asn Gly Lys Lys Glu Ala Gly Ile Pro Glu Phe Tyr Asp Tyr Asp
                565                 570                 575

Val Ala Leu Ile Lys Leu Lys Asn Lys Leu Lys Tyr Gly Gln Thr Ile
            580                 585                 590

Arg Pro Ile Cys Leu Pro Cys Thr Glu Gly Thr Thr Arg Ala Leu Arg
        595                 600                 605

Leu Pro Pro Thr Thr Thr Cys Gln Gln Gln Lys Glu Glu Leu Leu Pro
        610                 615                 620

Ala Gln Asp Ile Lys Ala Leu Phe Val Ser Glu Glu Lys Lys Leu
625                 630                 635                 640

Thr Arg Lys Glu Val Tyr Ile Lys Asn Gly Asp Lys Lys Gly Ser Cys
                645                 650                 655

Glu Arg Asp Ala Gln Tyr Ala Pro Gly Tyr Asp Lys Val Lys Asp Ile
            660                 665                 670

Ser Glu Val Val Thr Pro Arg Phe Leu Cys Thr Gly Gly Val Ser Pro
        675                 680                 685
```

```
Tyr Ala Asp Pro Asn Thr Cys Arg Gly Asp Ser Gly Gly Pro Leu Ile
        690             695             700

Val His Lys Arg Ser Arg Phe Ile Gln Val Gly Val Ile Ser Trp Gly
705             710             715             720

Val Val Asp Val Cys Lys Asn Gln Lys Arg Gln Lys Gln Val Pro Ala
                725             730             735

His Ala Arg Asp Phe His Ile Asn Leu Phe Gln Val Leu Pro Trp Leu
            740             745             750

Lys Glu Lys Leu Gln Asp Glu Asp Leu Gly Phe Leu
        755             760
```

METHODS OF INDUCING COMPLEMENT ACTIVITY

RELATED APPLICATIONS

This Application is a national stage filing under 35 U.S.C. 371 of International Patent Application Serial No. PCT/US2018/055444, filed Oct. 11, 2018, which claims priority to U.S. Provisional Application No. 62/637,135, filed Mar. 1, 2018 and to U.S. Provisional Application No. 62/570,953, filed Oct. 11, 2017. The entire contents of these applications are incorporated herein by reference.

FIELD OF THE DISCLOSURE

The present disclosure relates generally to the field of therapeutics complement-related disorders.

BACKGROUND

The complement system is part of the innate immune system. Its primary role is to "complement" the ability of antibodies and phagocytic cells to clear harmful pathogens from an organism.

The complement system includes three separate upstream activation pathways, all converging on a common terminal pathway. Two of the pathways are induced by specific and distinct mechanisms: the classical pathway (CP) is engaged when antibodies bind to antigens, and the lectin pathway (LP) is activated by carbohydrate residues on the surface of pathogens. The alternative pathway (AP) is unique in that it is continuously active at a basal level, referred to as "AP tick-over"; its activity can be greatly increased by a variety of signals on foreign surfaces and damaged cells via a positive-feedback amplification loop. The primary driver of the AP amplification loop is the AP convertase (C3bBb). This enzyme is formed when the zymogen factor B is cleaved to generate the split product fBb, which rapidly associates with surface-bound C3b to form active enzyme C3bBb. C3bBb then continues to cleave additional molecules of the central C3 protein, leading to the generation of opsonins (C3b, iC3b), anaphylatoxins (C3a and C5a) and the terminal lytic complex (MAC; C5b-9).

BRIEF SUMMARY

Certain aspects of the present disclosure are directed to a method of inducing a complement activity on a surface of a cell comprising contacting the cell with an effective amount of an antibody that specifically binds Factor Bb ("anti-Factor B antibody"), wherein the anti-Factor B antibody inhibits dissociation of a C3bBb complex. In some embodiments, the anti-Factor B antibody specifically binds Factor B in addition to Factor Bb.

In some embodiments, the anti-Factor B antibody has one or more properties selected from the group consisting of (i) specifically binds to a C3bBb complex, (ii) reduces, inhibits, or prevents degradation of a C3bBb complex, (iii) induces C3 cleavage in serum, (iv) reduces serum concentration of C3, (v) induces accumulation of C3b on the surface of the cell; (vi) induces the loss of serum complement activity, (vii) induces membrane attack deposition on the cell surface, and (viii) any combination thereof. In some embodiments, the anti-Factor B antibody reduces or blocks CD55-mediated dissociation of the C3bBb complex. In some embodiments, the anti-Factor B antibody reduces or blocks Factor-H-mediated dissociation of the C3bBb complex.

In some embodiments, the complement activity is a complement-mediated cell death. In some embodiments, the complement activity is an alternative complement pathway. In some embodiments, the cell is an in vivo cell.

In some embodiments, the anti-Factor B antibody competes for binding to the C3bBb complex with a reference antibody comprising a heavy chain variable region having SEQ ID NO: 7 and a light chain variable region having SEQ ID NO: 8. In some embodiments, the anti-Factor B antibody specifically binds to the same epitope on Factor Bb as a reference antibody comprising a heavy chain variable region having SEQ ID NO: 7 and a light chain variable region having SEQ ID NO: 8.

In some embodiments, the anti-Factor B antibody comprises a complementarity determining region-1 (CDR1), a CDR2, and a CDR3 of a heavy chain variable region (VH) and a CDR1, a CDR2, and a CDR3 of a light chain variable region (VL), wherein the VH CDR3 comprises SEQ ID NO: 3 or SEQ ID NO: 3 with one or two amino acid substitutions. In some embodiments, the anti-Factor B antibody comprises a CDR1, a CDR2, and a CDR3 of a heavy chain variable region (VH) and a CDR1, a CDR2, and a CDR3 of a light chain variable region (VL), wherein the VH CDR1 comprises SEQ ID NO: 1 or SEQ ID NO: 1 with one or two amino acid substitutions. In some embodiments, the anti-Factor B antibody comprises a CDR1, a CDR2, and a CDR3 of a heavy chain variable region (VH) and a CDR1, a CDR2, and a CDR3 of a light chain variable region (VL), wherein the VH CDR2 comprises SEQ ID NO: 2 or SEQ ID NO: 2 with one or two amino acid substitutions.

In some embodiments, the anti-Factor B antibody comprises a CDR1, a CDR2, and a CDR3 of a heavy chain variable region (VH) and a CDR1, a CDR2, and a CDR3 of a light chain variable region (VL), wherein the VL CDR1 comprises SEQ ID NO: 4 or SEQ ID NO: 4 with one or two amino acid substitutions. In some embodiments, the anti-Factor B antibody comprises a CDR1, a CDR2, and a CDR3 of a heavy chain variable region (VH) and a CDR1, a CDR2, and a CDR3 of a light chain variable region (VL), wherein the VL CDR2 comprises SEQ ID NO: 5 or SEQ ID NO: 5 with one or two amino acid substitutions. In some embodiments, the anti-Factor B antibody comprises a CDR1, a CDR2, and a CDR3 of a heavy chain variable region (VH) and a CDR1, a CDR2, and a CDR3 of a light chain variable region (VL), wherein the VL CDR3 comprises SEQ ID NO: 6 or SEQ ID NO: 6 with one or two amino acid substitutions.

In some embodiments, the VH of the anti-Factor B antibody comprises an amino acid sequence that is at least 80%, 85%, 90%, 95%, 96%, 97%, 98%, 99%, or 100% identical to SEQ ID NO: 7. In some embodiments, the VL of the anti-Factor B antibody comprises an amino acid sequence that is at least 80%, 85%, 90%, 95%, 96%, 97%, 98%, 99%, or 100% identical to SEQ ID NO: 8.

In some embodiments, the anti-Factor B antibody is a chimeric antibody, a humanized antibody, or a human antibody. In some embodiments, the anti-Factor B antibody is a bispecific or multispecific antibody.

In some embodiments, the anti-Factor B antibody treats a disease or condition by inducing cell death. In some embodiments, the disease or condition comprises a cancer, an infection, or an autoimmune disease. In some embodiments, the anti-Factor B antibody is administered parenterally, intravenously, subcutaneously, intradermally, transdermally, intramuscularly, orally, intraocularly, intrathecally, intraperitoneally, intranasally, buccally, sublingually, rectally, vaginally, or via pulmonary route.

Some aspects of the present disclosure are directed to a bispecific antibody comprising (i) an antigen binding domain that specifically binds Factor Bb ("an anti-Factor B binding domain") and inhibits dissociation of a C3bBb complex and (ii) a second antigen binding domain that is tissue or cell specific. In some embodiments, the anti-Factor B antibody specifically binds Factor B in addition to Factor Bb.

In some embodiments, the anti-Factor B binding domain has one or more properties selected from the group consisting of (i) specifically binds to a C3bBb complex, (ii) reduces, inhibits, or prevents degradation of a C3bBb complex, (iii) induces a complement activity, (iv) induces C3 cleavage in serum, (v) reduces serum concentration of C3, (vi) induces accumulation of C3b on the surface of the cell; (vii) induces membrane attack complex deposition on the cell surface, and (viii) any combination thereof.

In some embodiments, the anti-Factor B binding domain reduces or blocks CD55-mediated dissociation of the C3bBb complex. In some embodiments, the anti-Factor B binding domain reduces or blocks Factor-H-mediated dissociation of the C3bBb complex.

In some embodiments, the anti-Factor B binding domain competes for binding to the C3bBb complex with a reference antibody comprising a heavy chain variable region having SEQ ID NO: 7 and a light chain variable region having SEQ ID NO: 8. In some embodiments, the anti-Factor B binding domain specifically binds to the same epitope on Factor Bb as a reference antibody comprising a heavy chain variable region having SEQ ID NO: 7 and a light chain variable region having SEQ ID NO: 8.

In some embodiments, the anti-Factor B binding domain comprises a CDR1, a CDR2, and a CDR3 of a heavy chain variable region (VH) and a CDR1, a CDR2, and a CDR3 of a light chain variable region (VL), wherein the VH CDR3 comprises SEQ ID NO: 3 or SEQ ID NO: 3 with one or two amino acid substitutions. In some embodiments, the anti-Factor B binding domain comprises a CDR1, a CDR2, and a CDR3 of a heavy chain variable region (VH) and a CDR1, a CDR2, and a CDR3 of a light chain variable region (VL), wherein the VH CDR1 comprises SEQ ID NO: 1 or SEQ ID NO: 1 with one or two amino acid substitutions. In some embodiments, the anti-Factor B binding domain comprises a CDR1, a CDR2, and a CDR3 of a heavy chain variable region (VH) and a CDR1, a CDR2, and a CDR3 of a light chain variable region (VL), wherein the VH CDR2 comprises SEQ ID NO: 2 or SEQ ID NO: 2 with one or two amino acid substitutions.

In some embodiments, the anti-Factor B binding domain comprises a CDR1, a CDR2, and a CDR3 of a heavy chain variable region (VH) and a CDR1, a CDR2, and a CDR3 of a light chain variable region (VL), wherein the VL CDR1 comprises SEQ ID NO: 4 or SEQ ID NO: 4 with one or two amino acid substitutions. In some embodiments, the anti-Factor B binding domain comprises a CDR1, a CDR2, and a CDR3 of a heavy chain variable region (VH) and a CDR1, a CDR2, and a CDR3 of a light chain variable region (VL), wherein the VL CDR2 comprises SEQ ID NO: 5 or SEQ ID NO: 5 with one or two amino acid substitutions. In some embodiments, the anti-Factor B binding domain comprises a CDR1, a CDR2, and a CDR3 of a heavy chain variable region (VH) and a CDR1, a CDR2, and a CDR3 of a light chain variable region (VL), wherein the VL CDR3 comprises SEQ ID NO: 6 or SEQ ID NO: 6 with one or two amino acid substitutions.

In some embodiments, the VH of the anti-Factor B binding domain comprises an amino acid sequence that is at least 80%, 85%, 90%, 95%, 96%, 97%, 98%, 99%, or 100% identical to SEQ ID NO: 7. In some embodiments, the VL of the anti-Factor B binding domain comprises an amino acid sequence that is at least 80%, 85%, 90%, 95%, 96%, 97%, 98%, 99%, or 100% identical to SEQ ID NO: 8.

Some aspects of the present disclosure are directed to a multispecific antibody comprising (i) a bispecific antibody disclosed herein and (ii) a third antigen binding domain.

Some aspects of the present disclosure are directed to a polynucleotide or a set of polynucleotides encoding an antibody, a bispecific antibody, or a multi-specific antibody disclosed herein. Some aspects of the present disclosure are directed to a vector or a set of vectors comprising a polynucleotide or a set of polynucleotides disclosed herein.

Some aspects of the present disclosure are directed to a method of inducing a complement activity on a surface of a cell comprising contacting the cell with an effective amount of a bispecific antibody or a multispecific antibody disclosed herein. In some embodiments, the complement activity is a complement-mediated cell death.

Some aspects of the present disclosure are directed to a method of inducing cell death in a subject in need thereof comprising administering an effective amount of a bispecific antibody or a multispecific antibody disclosed herein.

Some aspects of the present disclosure are directed to a method of treating a disease or condition by inducing cell death in a subject in need thereof comprising administering an effective amount of a bispecific antibody or a multispecific antibody disclosed herein.

EMBODIMENTS

E1. A method of inducing a complement activity on a surface of a cell comprising contacting the cell with an effective amount of an antibody that specifically binds Factor Bb ("anti-Factor B antibody"), wherein the anti-Factor B antibody inhibits dissociation of a C3bBb complex.

E2. The method of E1, wherein the anti-Factor B antibody specifically binds Factor B in addition to Factor Bb.

E3. The method of E1 or E2, wherein the anti-Factor B antibody has one or more properties selected from the group consisting of (i) specifically binds to a C3bBb complex, (ii) reduces, inhibits, or prevents degradation of a C3bBb complex, (iii) induces C3 cleavage in serum, (iv) reduces serum concentration of C3, (v) induces accumulation of C3b on the surface of the cell; (vi) induces the loss of serum complement activity, (vii) induces membrane attack deposition on the cell surface, and (viii) any combination thereof.

E4. The method of any one of E1 to E3, wherein the anti-Factor B antibody reduces or blocks CD55-mediated dissociation of the C3bBb complex.

E5. The method of any one of E1 to E4, wherein the anti-Factor B antibody reduces or blocks Factor-H-mediated dissociation of the C3bBb complex.

E6. The method of any one of E1 to E5, wherein the complement activity is a complement-mediated cell death.

E7. The method of any one of E1 to E6, wherein the complement activity is an alternative complement pathway.

E8. The method of any one of E1 to E7, wherein the cell is an in vivo cell.

E9. The method of any one of E1 to E8, wherein the anti-Factor B antibody competes for binding to the C3bBb complex with a reference antibody comprising a heavy chain variable region having SEQ ID NO: 7 and a light chain variable region having SEQ ID NO: 8.

E10. The method of any one of E1 to E9, wherein the anti-Factor B antibody specifically binds to the same epitope on Factor Bb as a reference antibody comprising a heavy chain variable region having SEQ ID NO: 7 and a light chain variable region having SEQ ID NO: 8.

E11. The method of any one of E1 to E10, wherein the anti-Factor B antibody comprises a complementarity determining region-1 (CDR1), a CDR2, and a CDR3 of a heavy chain variable region (VH) and a CDR1, a CDR2, and a CDR3 of a light chain variable region (VL), wherein the VH CDR3 comprises SEQ ID NO: 3 or SEQ ID NO: 3 with one or two amino acid substitutions.

E12. The method of any one of E1 to E11, wherein the anti-Factor B antibody comprises a CDR1, a CDR2, and a CDR3 of a heavy chain variable region (VH) and a CDR1, a CDR2, and a CDR3 of a light chain variable region (VL), wherein the VH CDR1 comprises SEQ ID NO: 1 or SEQ ID NO: 1 with one or two amino acid substitutions.

E13. The method of any one of E1 to E12, wherein the anti-Factor B antibody comprises a CDR1, a CDR2, and a CDR3 of a heavy chain variable region (VH) and a CDR1, a CDR2, and a CDR3 of a light chain variable region (VL), wherein the VH CDR2 comprises SEQ ID NO: 2 or SEQ ID NO: 2 with one or two amino acid substitutions.

E14. The method of any one of E1 to E13, wherein the anti-Factor B antibody comprises a CDR1, a CDR2, and a CDR3 of a heavy chain variable region (VH) and a CDR1, a CDR2, and a CDR3 of a light chain variable region (VL), wherein the VL CDR1 comprises SEQ ID NO: 4 or SEQ ID NO: 4 with one or two amino acid substitutions.

E15. The method of any one of E1 to E14, wherein the anti-Factor B antibody comprises a CDR1, a CDR2, and a CDR3 of a heavy chain variable region (VH) and a CDR1, a CDR2, and a CDR3 of a light chain variable region (VL), wherein the VL CDR2 comprises SEQ ID NO: 5 or SEQ ID NO: 5 with one or two amino acid substitutions.

E16. The method of any one of E1 to E15, wherein the anti-Factor B antibody comprises a CDR1, a CDR2, and a CDR3 of a heavy chain variable region (VH) and a CDR1, a CDR2, and a CDR3 of a light chain variable region (VL), wherein the VL CDR3 comprises SEQ ID NO: 6 or SEQ ID NO: 6 with one or two amino acid substitutions.

E17. The method of any one of E11 to E16, wherein the VH of the anti-Factor B antibody comprises an amino acid sequence that is at least 80%, 85%, 90%, 95%, 96%, 97%, 98%, 99%, or 100% identical to SEQ ID NO: 7.

E18. The method of any one of E11 to E17, wherein the VL of the anti-Factor B antibody comprises an amino acid sequence that is at least 80%, 85%, 90%, 95%, 96%, 97%, 98%, 99%, or 100% identical to SEQ ID NO: 8.

E19. The method of any one of E1 to E18, wherein the anti-Factor B antibody is a chimeric antibody, a humanized antibody, or a human antibody.

E20. The method of any one of E1 to E19, wherein the anti-Factor B antibody is a bispecific or multispecific antibody.

E21. The method of any one of E1 to E20, wherein the anti-Factor B antibody treats a disease or condition by inducing cell death.

E22. The method of E21, wherein the disease or condition comprises a cancer, an infection, or an autoimmune disease.

E23. The method of E22, wherein the cancer is selected from the group consisting of melanoma (MEL); renal cell carcinoma (RCC); lung cancer; colorectal cancer (CRC); prostate cancer; liver cancer; squamous cell carcinoma of the head and neck; carcinomas of the esophagus, ovary, gastrointestinal tract, and breast; a hematologic malignancy such as multiple myeloma, B-cell lymphoma, T-cell lymphoma, Hodgkin's lymphoma/primary mediastinal B-cell lymphoma, and chronic myelogenous leukemia; and any combination thereof.

E24. The method of E22, wherein the autoimmune disease is selected from the group consisting of multiple sclerosis, type 1 diabetes, rheumatoid arthritis, lupus, celiac disease, Sjorgren's syndrome, polymyalgia, ankylosing spondylitis, alopecia areata, vasculitis, temporal arteritis, Addison's disease, age-related macular degeneration, alopecia, autoimmune hepatitis (e.g., autoimmune hepatitis associated with hepatitis B virus infection; autoimmune hepatitis associated with hepatitis C virus infection), autoimmune hemolytic anemia, autoimmune skin diseases, autoimmune thyroid disease, bullous pemphigoid, celiac disease, cold agglutinin disease, dermatomyositis, type 1 diabetes mellitus, Grave's disease, Goodpasture's syndrome, Hashimoto's disease, hypoparathyroidism, hypopituitarism, hypothyroidism, idiopathic thrombocytopenic purpura, inflammatory bowel disease (e.g., Crohn's disease; ulcerative colitis), multiple sclerosis, myasthenia gravis, myocarditis, neuromyelitis optica, pemphigus vulgaris, pemphigus foliaceus, polymyositis, psoriasis, rheumatoid arthritis, sarcoidosis, scleroderma, Sjogren's syndrome, systemic lupus erythematosus, uveitis, Wegener's granulomatosis and poly/dermatomyositis, age-related autoimmune disorders, age-related macular degeneration, Alzheimer's disease, amyotrophic lateral sclerosis, anaphylaxis, argyrophilic grain dementia, arthritis (e.g., rheumatoid arthritis), asthma, atherosclerosis, atypical hemolytic uremic syndrome, autoimmune diseases, autoimmune hemolytic anemia, Barraquer-Simons syndrome, Behcet's disease, British type amyloid angiopathy, bullous pemphigoid, Buerger's disease, C1q nephropathy, cancer, catastrophic antiphospholipid syndrome, cerebral amyloid angiopathy, cold agglutinin disease, corticobasal degeneration, Creutzfeldt-Jakob disease, Crohn's disease, cryoglobulinemic vasculitis, dementia pugilistica, dementia with Lewy Bodies (DLB), diffuse neurofibrillary tangles with calcification, Discoid lupus erythematosus, Down's syndrome, focal segmental glomerulosclerosis, formal thought disorder, frontotemporal dementia (FTD), frontotemporal dementia with parkinsonism linked to chromosome 17, frontotemporal lobar degeneration, Gerstmann-Straussler-Scheinker disease, Guillain-Barre syndrome, Hallervorden-Spatz disease, hemolytic-uremic syndrome, hereditary angioedema, hypophosphastasis, idiopathic pneumonia syndrome, immune complex diseases, inclusion body myositis, inflammatory disease, ischemia/reperfusion injury, mild cognitive impairment, immunothrombocytopenic purpura (ITP), molybdenum cofactor deficiency (MoCD) type A, membranoproliferative glomerulonephritis (MPGN) I, membranoproliferative glomerulonephritis (MPGN) II (dense deposit disease), membranous nephritis, multi-infarct dementia, lupus (e.g., systemic lupus erythematosus (SLE)), glomerulonephritis, Kawasaki disease, multifocal motor neuropathy, multiple sclerosis, multiple system atrophy, myasthenia gravis, myocardial infarction, myotonic dystrophy, neuromyelitis optica, Niemann-Pick disease type C, non-Guamanian motor neuron disease with neurofibrillary tangles, Parkinson's disease, Parkinson's disease with dementia, paroxysmal nocturnal hemoglobinuria, Pemphigus vulgaris, Pick's disease, postencephalitic parkinsonism, polymyositis, prion protein cerebral amyloid angiopathy, progressive subcortical gliosis, progressive supranuclear palsy, psoriasis, sepsis, Shiga-toxin *E coli* (STEC)-HuS, spinal muscular atrophy, stroke, subacute sclerosing panencephalitis, Tangle only dementia, transplant rejection, vasculitis (e.g., ANCA associated vasculitis), Wegner's granulomatosis, sickle cell disease, cryoglobulinemia, mixed cryoglobulinemia, essential mixed cryoglobulinemia, Type II mixed cryoglobulinemia, Type III mixed cryoglobulinemia, nephritis, drug-induced thrombocytopenia, lupus nephritis, bullous pemphigoid, Epidermolysis bullosa acquisita, delayed hemolytic transfusion reaction, hypocomplementemic urticarial vasculitis syndrome, pseudophakic bullous keratopathy, platelet refractoriness and any combination thereof.

E25. The method of E22, wherein the infection comprises a bacterial infection (e.g., *Neisseria meningitidis* or *Streptococcus*), a viral infection (e.g., HIV), a fungal infection, a parasitic infection, or any combination thereof.

E26. The method of any one of E1 to E25, wherein the anti-Factor B antibody is administered parenterally, intravenously, subcutaneously, intradermally, transdermally, intramuscularly, orally, intraocularly, intrathecally, intraperitoneally, intranasally, buccally, sublingually, rectally, vaginally, or via pulmonary route.

E27. The method of any one of E1 to E26, wherein the cell is a tumor cell or a pathogen.

E28. The method of any one of E1 to E27, wherein the cell is a native cell.

E29. A bispecific antibody comprising (i) an antigen binding domain that specifically binds Factor Bb ("an anti-Factor B binding domain") and inhibits dissociation of a C3bBb complex and (ii) a second antigen binding domain that is tissue or cell specific.

E30. The bispecific antibody of E29, wherein the anti-Factor B antibody specifically binds Factor B in addition to Factor Bb.

E31. The bispecific antibody of E29 or E30, wherein the anti-Factor B binding domain has one or more properties selected from the group consisting of (i) specifically binds to a C3bBb complex, (ii) reduces, inhibits, or prevents degradation of a C3bBb complex, (iii) induces a complement activity, (iv) induces C3 cleavage in serum, (v) reduces serum concentration of C3, (vi) induces accumulation of C3b on the surface of the cell; (vii) induces membrane attack complex deposition on the cell surface, and (viii) any combination thereof.

E32. The bispecific antibody of any one of E29 to E31, wherein the anti-Factor B binding domain reduces or blocks CD55-mediated dissociation of the C3bBb complex.

E33. The bispecific antibody of any one of E29 to E32, wherein the anti-Factor B binding domain reduces or blocks Factor-H-mediated dissociation of the C3bBb complex.

E34. The bispecific antibody of any one of E29 to E33, wherein the anti-Factor B binding domain competes for binding to the C3bBb complex with a reference antibody comprising a heavy chain variable region having SEQ ID NO: 7 and a light chain variable region having SEQ ID NO: 8.

E35. The bispecific antibody of any one of E29 to E34, wherein the anti-Factor B binding domain specifically binds to the same epitope on Factor Bb as a reference antibody comprising a heavy chain variable region having SEQ ID NO: 7 and a light chain variable region having SEQ ID NO: 8.

E36. The bispecific antibody of any one of E29 to E35, wherein the anti-Factor B binding domain comprises a CDR1, a CDR2, and a CDR3 of a heavy chain variable region (VH) and a CDR1, a CDR2, and a CDR3 of a light chain variable region (VL), wherein the VH CDR3 comprises SEQ ID NO: 3 or SEQ ID NO: 3 with one or two amino acid substitutions.

E37. The bispecific antibody of any one of E29 to E36, wherein the anti-Factor B binding domain comprises a CDR1, a CDR2, and a CDR3 of a heavy chain variable region (VH) and a CDR1, a CDR2, and a CDR3 of a light chain variable region (VL), wherein the VH CDR1 comprises SEQ ID NO: 1 or SEQ ID NO: 1 with one or two amino acid substitutions.

E38. The bispecific antibody of any one of E29 to E37, wherein the anti-Factor B binding domain comprises a CDR1, a CDR2, and a CDR3 of a heavy chain variable region (VH) and a CDR1, a CDR2, and a CDR3 of a light chain variable region (VL), wherein the VH CDR2 comprises SEQ ID NO: 2 or SEQ ID NO: 2 with one or two amino acid substitutions.

E39. The bispecific antibody of any one of E29 to E38, wherein the anti-Factor B binding domain comprises a CDR1, a CDR2, and a CDR3 of a heavy chain variable region (VH) and a CDR1, a CDR2, and a CDR3 of a light chain variable region (VL), wherein the VL CDR1 comprises SEQ ID NO: 4 or SEQ ID NO: 4 with one or two amino acid substitutions.

E40. The bispecific antibody of any one of E29 to E39, wherein the anti-Factor B binding domain comprises a CDR1, a CDR2, and a CDR3 of a heavy chain variable region (VH) and a CDR1, a CDR2, and a CDR3 of a light chain variable region (VL), wherein the VL CDR2 comprises SEQ ID NO: 5 or SEQ ID NO: 5 with one or two amino acid substitutions.

E41. The bispecific antibody of any one of E29 to E40, wherein the anti-Factor B binding domain comprises a CDR1, a CDR2, and a CDR3 of a heavy chain variable region (VH) and a CDR1, a CDR2, and a CDR3 of a light chain variable region (VL), wherein the VL CDR3 comprises SEQ ID NO: 6 or SEQ ID NO: 6 with one or two amino acid substitutions.

E42. The bispecific antibody of any one of E36 to E41, wherein the VH of the anti-Factor B binding domain comprises an amino acid sequence that is at least 80%, 85%, 90%, 95%, 96%, 97%, 98%, 99%, or 100% identical to SEQ ID NO: 7.

E43. The bispecific antibody of any one of E36 to E42, wherein the VL of the anti-Factor B binding domain comprises an amino acid sequence that is at least 80%, 85%, 90%, 95%, 96%, 97%, 98%, 99%, or 100% identical to SEQ ID NO: 8.

E44. The bispecific antibody of any one of E29 to E42, which is chimeric or humanized.

E45. A multispecific antibody comprising (i) the bispecific antibody of any one of E29 to E44 and (ii) a third antigen binding domain.

E46. A composition comprising the bispecific antibody of any one of E29 to E44 or the multispecific antibody of E44.

E47. A polynucleotide or a set of polynucleotides comprising a nucleic acid encoding the bispecific antibody of any one of E29 to E44 or the multispecific antibody of E45.

E48. A vector or a set of vectors comprising the polynucleotide or the set of polynucleotides of E47.

E49. The vector or the set of vectors of E48, wherein the polynucleotide or the set of polynucleotides is operably linked to a promoter.

E50. A host cell comprising the polynucleotide or the set of polynucleotides of E45 or the vector of the set of vectors of E48 or E49.

E51. A method of producing a bispecific antibody or multispecific antibody comprising culturing the host cell of E50 under suitable conditions.

E52. A method of inducing a complement activity on a surface of a cell comprising contacting the cell with an effective amount of the bispecific antibody of any one of E29 to E44 or the multispecific antibody of E45.

E53. The method of E52, wherein the complement activity is a complement-mediated cell death.

E54. The method of E52 or E53, wherein the complement activity is an alternative complement pathway.

E55. The method of any one of E52 to E54, wherein the cell is an in vivo cell.

E56. A method of inducing cell death in a subject in need thereof comprising administering an effective amount of the bispecific antibody of any one of E29 to E44 or the multispecific antibody of E45.

E57. A method of treating a disease or condition by inducing cell death in a subject in need thereof comprising administering an effective amount of the bispecific antibody of any one of E29 to E44 or the multispecific antibody of E45.

E58. The method of E57, wherein the disease or condition comprises a cancer, and infection, or an autoimmune disease.

E59. The method of E58, wherein the cancer is selected from the group consisting of melanoma (MEL); renal cell carcinoma (RCC); lung cancer; colorectal cancer (CRC); prostate cancer; liver cancer; squamous cell carcinoma of the head and neck; carcinomas of the esophagus, ovary, gastrointestinal tract, and breast; a hematologic malignancy such as multiple myeloma, B-cell lymphoma, T-cell lymphoma, Hodgkin's lymphoma/primary mediastinal B-cell lymphoma, and chronic myelogenous leukemia; and any combination thereof.

E60. The method of E59, wherein the infection comprises a bacterial infection (e.g., Neisseria meningitidis or Streptococcus), a viral infection (e.g., HIV), a fungal infection, a parasitic infection, or any combination thereof.

E61. The method of E58, wherein the autoimmune disease is selected from the group consisting of multiple sclerosis, type 1 diabetes, rheumatoid arthritis, lupus, celiac disease, Sjorgren's syndrome, polymyalgia, ankylosing spondylitis, alopecia areata, vasculitis, temporal arteritis, Addison's disease, age-related macular degeneration, alopecia, autoimmune hepatitis (e.g., autoimmune hepatitis associated with hepatitis B virus infection; autoimmune hepatitis associated with hepatitis C virus infection), autoimmune hemolytic anemia, autoimmune skin diseases, autoimmune thyroid disease, bullous pemphigoid, celiac disease, cold agglutinin disease, dermatomyositis, type 1 diabetes mellitus, Grave's disease, Goodpasture's syndrome, Hashimoto's disease, hypoparathyroidism, hypopituitarism, hypothyroidism, idiopathic thrombocytopenic purpura, inflammatory bowel disease (e.g., Crohn's disease; ulcerative colitis), multiple sclerosis, myasthenia gravis, myocarditis, neuromyelitis optica, pemphigus vulgaris, pemphigus foliaceus, polymyositis, psoriasis, rheumatoid arthritis, sarcoidosis, scleroderma, Sjogren's syndrome, systemic lupus erythematosus, uveitis, Wegener's granulomatosis and poly/dermatomyositis, age-related autoimmune disorders, age-related macular degeneration, Alzheimer's disease, amyotrophic lateral sclerosis, anaphylaxis, argyrophilic grain dementia, arthritis (e.g., rheumatoid arthritis), asthma, atherosclerosis, atypical hemolytic uremic syndrome, autoimmune diseases, autoimmune hemolytic anemia, Barraquer-Simons syndrome, Behcet's disease, British type amyloid angiopathy, bullous pemphigoid, Buerger's disease, Clq nephropathy, cancer, catastrophic antiphospholipid syndrome, cerebral amyloid angiopathy, cold agglutinin disease, corticobasal degeneration, Creutzfeldt-Jakob disease, Crohn's disease, cryoglobulinemic vasculitis, dementia pugilistica, dementia with Lewy Bodies (DLB), diffuse neurofibrillary tangles with calcification, Discoid lupus erythematosus, Down's syndrome, focal segmental glomerulosclerosis, formal thought disorder, frontotemporal dementia (FTD), frontotemporal dementia with parkinsonism linked to chromosome 17, frontotemporal lobar degeneration, Gerstmann-Straussler-Scheinker disease, Guillain-Barre syndrome, Hallervorden-Spatz disease, hemolytic-uremic syndrome, hereditary angioedema, hypophosphastasis, idiopathic pneumonia syndrome, immune complex diseases, inclusion body myositis, inflammatory disease, ischemia/reperfusion injury, mild cognitive impairment, immunothrombocytopenic purpura (ITP), molybdenum cofactor deficiency (MoCD) type A, membranoproliferative glomerulonephritis (MPGN) I, membranoproliferative glomerulonephritis (MPGN) II (dense deposit disease), membranous nephritis, multi-infarct dementia, lupus (e.g., systemic lupus erythematosus (SLE)), glomerulonephritis, Kawasaki disease, multifocal motor neuropathy, multiple sclerosis, multiple system atrophy, myasthenia gravis, myocardial infarction, myotonic dystrophy, neuromyelitis optica, Niemann-Pick disease type C, non-Guamanian motor neuron disease with neurofibrillary tangles, Parkinson's disease, Parkinson's disease with dementia, paroxysmal nocturnal hemoglobinuria, Pemphigus vulgaris, Pick's disease, postencephalitic parkinsonism, polymyositis, prion protein cerebral amyloid angiopathy, progressive subcortical gliosis, progressive supranuclear palsy, psoriasis, sepsis, Shiga-toxin *E coli* (STEC)-HuS, spinal muscular atrophy, stroke, subacute sclerosing panencephalitis, Tangle only dementia, transplant rejection, vasculitis (e.g., ANCA associated vasculitis), Wegner's granulomatosis, sickle cell disease, cryoglobulinemia, mixed cryoglobulinemia, essential mixed cryoglobulinemia, Type II mixed cryoglobulinemia, Type III mixed cryoglobulinemia, nephritis, drug-induced thrombocytopenia, lupus nephritis, bullous pemphigoid, Epidermolysis bullosa acquisita, delayed hemolytic transfusion reaction, hypocomplementemic urticarial vasculitis syndrome, pseudophakic bullous keratopathy, platelet refractoriness and any combination thereof.

BRIEF DESCRIPTION OF THE FIGURES

FIGS. 1A-1B are a graphical representations of Factor H (FIG. 1A) and DAF/CD55 (FIG. 1B) dissociation of C3bBb in human serum incubated with an anti-Factor B antibody (anti-Factor B Ab or also referred to as FBb Ab), which comprises a heavy chain variable region of SEQ ID NO: 7 and a light chain variable region of SEQ ID NO: 8. C3bBb complex load mixed with antibodies or antibody fragments (anti-Factor B Ab; anti-Factor B F(ab')$_2$; Quidel α-fB; anti-Factor B Fab; C3bBb) was added to Octet probes coated with Streptavidin. C3b+fB and fB were used as negative controls. At 600 seconds, the probe was transferred to a solution containing only buffer. Factor H (FIG. 1A) or DAF/CD55 (FIG. 1B) was added at 780 seconds. anti-Factor B F(ab')$_2$=F(ab')2 fragment of anti-Factor B Ab; Quidel α-fB=commercially available Factor B antibody; anti-Factor B Fab=Fab fragment of anti-Factor B Ab; fB=Factor B.

Buffer alone (lanes 2 and 3) and samples incubated with mIgG2a (lanes 4-6) were used as negative controls. Buffer: 10% normal human serum (NHS) in complement alternative pathway (CAP) dilution buffer. kD: kiloDaltons; mIgG2a: IgG2a monoclonal antibody; anti-Factor B Ab: Fab: Fab fragment of anti-Factor B Ab; Quidel α-fB: commercially available factor B antibody.

Figure 3:
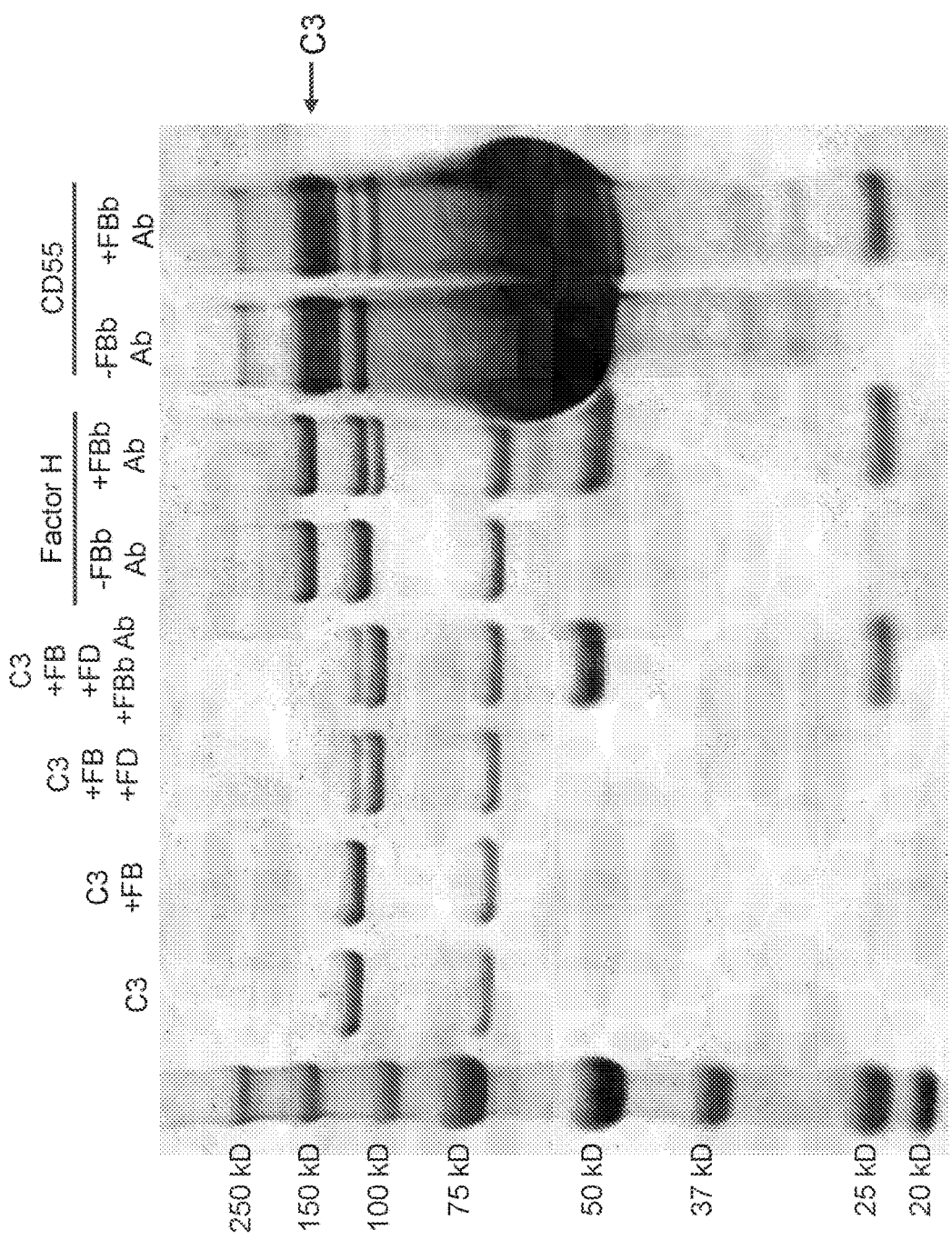

FIG. 3 is an image of a Coomassie gel detecting C3 cleavage in serum samples treated with one or more of C3, Factor B (FB), anti-Factor B Ab, Factor H, and DAF/CD55 followed by treatment with factor D, as indicated. Human C3 is normally detected at about 140 kD. kD: kiloDaltons.

Figure 4:
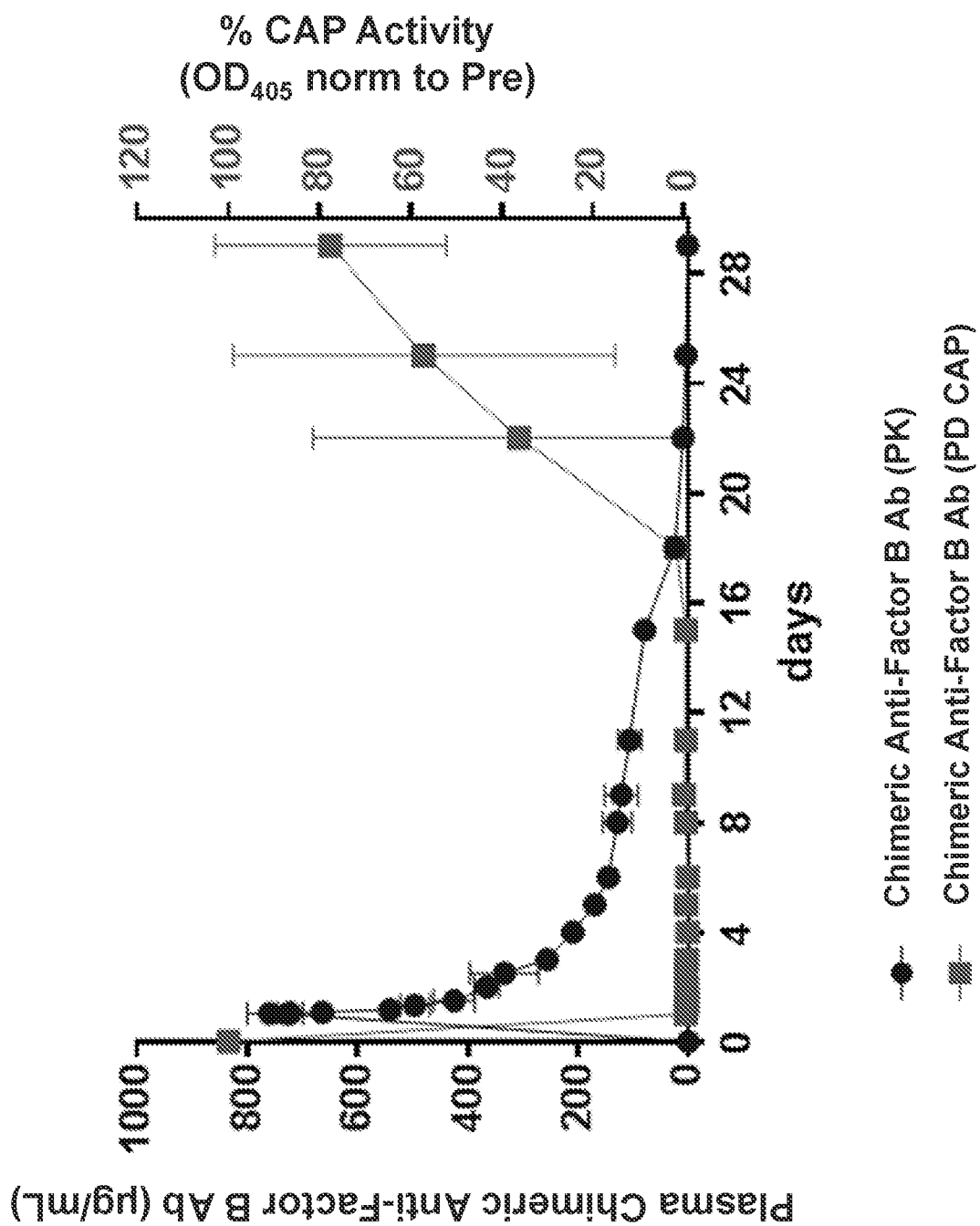

FIG. 4 is a graphical representation of the pharmacokinetics (PK) and pharmacodynamics (PD) of chimeric anti-Factor B Ab, comprising a heavy chain of SEQ ID NO: 12 and a light chain of SEQ ID NO: 13) in cynomolgus monkeys. Serum samples were taken at various time points as indicated on the x-axis. The concentration of chimeric anti-Factor B Ab in plasma (left Y-axis; circle time points) was measured over the 30 day period. Percent PD complement alternative pathway (CAP) activity (right Y-axis; square time points), measured over the 30 day period, was normalized to a pre-treatment baseline level.

DETAILED DESCRIPTION

The present disclosure provides methods of utilizing complement pathway to induce death of unwanted cells. In particular embodiment, the present disclosure include methods of inducing a complement activity on a surface of a cell comprising contacting the cell with an effective amount of an anti-Factor B antibody. In certain embodiments, the anti-Factor B antibody inhibits dissociation of a C3bBb complex. In some aspects, the anti-Factor B antibody is a bispecific antibody or a multispecific antibody.

I. Definitions

It is to be noted that the term "a" or "an" entity refers to one or more of that entity;

for example, "a nucleotide sequence," is understood to represent one or more nucleotide sequences. As such, the terms "a" (or "an"), "one or more," and "at least one" can be used interchangeably herein.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

The term "about" is used herein to mean approximately, roughly, around, or in the regions of When the term "about" is used in conjunction with a numerical range, it modifies that range by extending the boundaries above and below the numerical values set forth. Thus, "about 10-20" means "about 10 to about 20." In general, the term "about" can modify a numerical value above and below the stated value by a variance of, e.g., 10 percent, up or down (higher or lower).

An "antibody" includes, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as VH) and a heavy chain constant region. The heavy chain constant region comprises three constant domains, $C_{H1}$, $C_{H2}$ and $C_{H3}$. Each light chain comprises a light chain variable region (abbreviated herein as VL) and a light chain constant region. The light chain constant region comprises one constant domain, $C_L$. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody. An antigen-binding fragment of an antibody can include any portion of an antibody that retains the ability to bind the target of the antibody. In some embodiments, an antigen-binding fragment of an anti-Factor B antibody retains the ability to bind Factor Bb. In some embodiments, an antigen-binding fragment of an antibody comprises 1, 2, 3, 4, 5, or 6 CDRs of the antibody. In some embodiments, an antigen-binding fragment of an antibody comprises 1, 2, 3, 4, 5, or 6 CDRs and 1, 2, 3, 4, 5, 6, 7, or 8 framework regions of the antibody. In some embodiments, an antigen-binding fragment of an antibody comprises a VH region and/or a VL region of the antibody. Small additions, deletions, insertions, substitutions or modifications of amino acids are permissible as long as they do not abrogate the ability of the antibody to bind to a particular antigen. In particular, conservative amino acid substitutions in one or more framework region of the antibody are within the scope of the present disclosure.

The term "monoclonal antibody" ("mAb") refers to a non-naturally occurring antibody molecule of single molecular composition, i.e., antibody molecules whose primary sequences are essentially identical, and which exhibits a single binding specificity and affinity for a particular epitope. A mAb is an example of an isolated antibody. The term "monoclonal antibody" is not limited to antibodies prepared using hybridoma techniques. Rather, monoclonal antibodies, as used herein, can be produced by hybridoma, recombinant, transgenic or other techniques known to those skilled in the art.

A "bispecific" antibody, as used herein, refers to an antibody that is capable of binding two antigens. A "multispecific" antibody, as used herein, refers to an antibody that is capable of binding three or more antigens. In some embodiments, the bispecific antibody or the multispecific antibody comprises a first VH region, a first VL region, a second VH region, and a second VL region, wherein the first VH region and the first VL region bind Factor Bb, and the second VH region and the second VL region bind a second antigen. In some embodiments, the second antigen is a tumor antigen, e.g., an antigen present on the surface of a tumor cell. In some embodiments, the tumor antigen is selected from the group consisting of alphafetoprotein (AFP), carcinoembryonic antigen (CEA), CA-125, mucin 1 (MUC-1), epithelial tumor antigen (ETA), melanoma-associated antigen (MAGE), p53, an epidermal growth factor receptor (EGFR, e.g., HER2 and/or EGFR12), CD30, and any combination thereof. In some embodiments, the second antigen is an antigen present on a B cell, e.g., cluster of differentiation 19 (CD19) or CD20.

The term "binding" refers to a direct association between two molecules, due to, for example, covalent, electrostatic, hydrophobic, and ionic and/or hydrogen-bond interactions, including interactions such as salt bridges and water bridges. An anti-Factor B antibody of the present disclosure binds specifically to an epitope within Factor Bb protein. "Specific binding" refers to binding with an affinity of at least about $10^{-7}$ M or greater, e.g., $5 \times 10^{-7}$ M, $10^{-8}$ M, $5 \times 10^{-8}$ M, and greater. "Non-specific binding" refers to binding with an affinity of more than about $10^{-7}$ M, e.g., binding with an affinity of $10^{-6}$ M, $10^{-5}$ M, $10^{-4}$ M, etc. In some embodiments, the anti-Factor B antibody binds Factor Bb with an affinity of at least about $10^{-7}$ M, at least about $5 \times 10^{-7}$ M, $10^{-8}$ M, $5 \times 10^{-8}$ M, or more.

The terms "cross competes" and "cross competition," as used herein, refer to the ability of an antibody to compete for binding to a target antigen with a reference antibody. Any methods known in the art can be used to determine whether an antibody cross competes with a reference antibody. For example, BIAcore analysis, ELISA assays, or flow cytometry can be used to demonstrate cross-competition with the antibodies of the current invention. The ability of a test antibody to inhibit the binding of an antibody to Factor Bb demonstrates that the test antibody can compete with a reference antibody for binding to Factor Bb. In some embodiments, an antibody that cross competes with a reference antibody for binding to an antigen, e.g., Factor Bb, binds the same epitope as the reference antibody. In some embodiments, an antibody that cross competes with a reference antibody for binding to an antigen, e.g., Factor Bb, binds an epitope that is near or adjacent to the epitope recognized by the reference antibody. In some embodiments, an antibody that cross competes with a reference antibody for binding to an antigen, e.g., Factor Bb, binds an epitope that is distal to the epitope recognized by the reference antibody; however, binding of the antibody to the distal epitope is sufficient to disrupt the binding ability of the reference antibody to the antigen. An antibody binds the same epitope as a reference antibody if the antibody interacts with amino acid residues on the antigen which are the same as or overlap with the amino acids on the antigen that interact with the reference antibody.

"Administering," as used herein, means to give a pharmaceutically acceptable amount of an anti-Factor B antibody disclosed herein to a subject via a pharmaceutically acceptable route. Routes of administration can be intravenous, e.g., intravenous injection and intravenous infusion. Additional routes of administration include, e.g., subcutaneous, intramuscular, oral, nasal, and pulmonary administration. Anti-Factor B antibodies can be administered as part of a pharmaceutical composition comprising at least one excipient. In some embodiments, the anti-Factor B antibody is administered intravenously. In some embodiments, the anti-Factor B antibody is administered subcutaneously.

"Treat," "treatment," or "treating," as used herein refers to, e.g., the reduction in severity of a disease or condition; the reduction in the duration of a condition course; the amelioration or elimination of one or more symptoms associated with a disease or condition; the provision of beneficial effects to a subject with a disease or condition, without necessarily curing the disease or condition. In some embodiments, the term "treat" or "treating" means inducing complement activity in a subject in need thereof.

The term "induce a complement activity," as used herein, means to activate, increase, or prevent the termination of the complement pathway in a subject. The complement system includes three separate upstream activation pathways, all converging on a common terminal pathway. Two of the pathways are induced by specific and distinct mechanisms: the classical pathway (CP) is engaged when antibodies bind to antigens, and the lectin pathway (LP) is activated by carbohydrate residues on the surface of pathogens. The alternative pathway (AP) is unique in that it is continuously active at a basal level, referred to as "AP tick-over"; its activity can be greatly increased by a variety of signals on foreign surfaces and damaged cells via a positive-feedback amplification loop. The AP commences by the spontaneous hydrolysis of complement component C3. C3($H_2O$) then binds Factor B (SEQ ID NO: 15; Table 1), which is subsequently cleaved by Factor D to yield C3($H_2O$)Bb and Ba (a byproduct). C3($H_2O$)Bb then cleaves C3 into C3b (the active form of C3) and C3a (a byproduct). C3b then associates with Factor B, which is subsequently cleaved by Factor D, yielding C3bBb ("C3 convertase"). C3 convertase then continues to cleave additional molecules of the central C3 protein, leading to the generation of opsonins (C3b, iC3b), which facilitate phagocytosis; anaphylatoxins (C3a and C5a), which facilitate targeting of immune cells; and the terminal lytic complex (MAC; C5b-9), which damages the plasma membrane of a target cell, facilitating cell death. Induction of complement activity, as disclosed herein, can refer to activation or promotion of any step of the CP, LP, and or AP.

TABLE 1

Human Factor Bb Amino Acid Sequence

MGSNLSPQLCLMPFILGLLSGGVTTTPWSLARPQGSCSLEGVEIKGGSFR

LLQEGQALEYVCPSGFYPYPVQTRTCRSTGSWSTLKTQDQKTVRKAECRA

IHCPRPHDFENGEYWPRSPYYNVSDEISFHCYDGYTLRGSANRTCQVNGR

WSGQTAICDNGAGYCSNPGIPIGTRKVGSQYRLEDSVTYHCSRGLTLRGS

QRRTCQEGGSWSGTEPSCQDSFMYDTPQEVAEAFLSSLTETIEGVDAEDG

HGPGEQQKRKIVLDPSGSMNIYLVLDGSDSIGASNFTGAKKCLVNLIEKV

ASYGVKPRYGLVTYATYPKIWVKVSEADSSNADWVTKQLNEINYEDHKLK

SGTNTKKALQAVYSMMSWPDDVPPEGWNRTRHVIILMTDGLHNMGGDPIT

VIDEIRDLLYIGKDRKNPREDYLDVYVEGVGPLVNQVNINALASKKDNEQ

HVFKVKDMENLEDVFYQMIDESQSLSLCGMVWEHRKGTDYHKQPWQAKIS

VIRPSKGHESCMGAVVSEYFVLTAAHCFTVDDKEHSIKVSVGGEKRDLEI

EVVLFHPNYNINGKKEAGIPEFYDYDVALIKLKNKLKYGQTIRPICLPCT

EGTTRALRLPPTTTCQQQKEELLPAQDIKALFVSEEEKKLTRKEVYIKNG

DKKGSCERDAQYAPGYDKVKDISEVVTPRFLCTGGVSPYADPNTCRGDSG

GPLIVHKRSRFIQVGVISWGVVDVCKNQKRQKQVPAHARDFHINLFQVLP

WLKEKLQDEDLGFL (SEQ ID NO: 15)

In certain embodiments, the induction of complement activity comprises inhibiting an inhibitor of a complement component. Various checks and balances exist to prevent over-activation of the complement pathway. For example, membrane-bound proteins including complement receptor 1 (CR1) and decay-accelerating factor ("DAF" or "CD55") compete with Factor B for binding to C3b on the cell surface, and both CR1 and DAF/CD55 are capable of displacing Bb from a C3bBb complex. Factor H similarly binds C3b prevent Factor B binding or to displace Factor Bb from a C3bBb complex. In some embodiments, the anti-Factor B antibody prevents displacement of the Bb from a C3bBb complex by CR1, DAF/CD55, and/or Factor H.

"Subject," as used herein means a human individual. Subject can be a patient who is currently suffering from a disease or a condition. In certain embodiments, the disease or condition comprises a cancer or an autoimmune disease. In some embodiments, the cancer is selected from the group consisting of melanoma (MEL); renal cell carcinoma (RCC); lung cancer; colorectal cancer (CRC); prostate cancer; liver cancer; squamous cell carcinoma of the head and neck; carcinomas of the esophagus, ovary, gastrointestinal tract, and breast; a hematologic malignancy such as multiple myeloma, B-cell lymphoma, T-cell lymphoma, Hodgkin's lymphoma/primary mediastinal B-cell lymphoma, and chronic myelogenous leukemia; and any combination thereof. In some embodiments, the autoimmune disease is selected from the group consisting of multiple sclerosis, type 1 diabetes, rheumatoid arthritis, lupus, celiac disease, Sjorgren's syndrome, polymyalgia, ankylosing spondylitis, alopecia areata, vasculitis, temporal arteritis, and any combination thereof. In some embodiments, the disease or disorder comprises an infection by a pathogen. In some embodiments, the pathogen is selected from a bacterium, a parasite, a fungus, or any combination thereof.

A "therapeutic dose," "dose," "effective dose," or "dosing amount" as used (interchangeably) herein, means a dose that achieves a therapeutic goal, as described herein. In some embodiments, a "therapeutic dose" means a dose that induces complement activity in a subject. In certain embodiments, a "therapeutic dose" means a dose that induces complement activity and results in targeted cell death in a subject.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another embodiment, a string of amino acids can be conservatively replaced with a structurally similar string that differs in order and/or composition of side chain family members.

The term "percent sequence identity" between two polynucleotide or polypeptide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences may be accomplished using readily available software both for online use and for download. Suitable software programs are available from various sources, and for alignment of both protein and nucleotide sequences. One suitable program to determine percent sequence identity is bl2seq, part of the BLAST suite of programs available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity may be curated either automatically or manually.

The polynucleotide variants can contain alterations in the coding regions, non-coding regions, or both. In one embodiment, the polynucleotide variants contain alterations which produce silent substitutions, additions, or deletions, but do not alter the properties or activities of the encoded polypeptide. In another embodiment, nucleotide variants are produced by silent substitutions due to the degeneracy of the genetic code. In other embodiments, variants in which 5-10, 1-5, or 1-2 amino acids are substituted, deleted, or added in any combination. Polynucleotide variants can be produced for a variety of reasons, e.g., to optimize codon expression for a particular host (change codons in the human mRNA to others, e.g., a bacterial host such as *E. coli*).

II. Methods of the Disclosure

The present disclosure is directed to methods of inducing complement activity on a surface of a cell comprising contacting the cell with an effective amount of an anti-Factor B antibody. The anti-Factor B antibody can bind to Factor B, which often circulates in the blood as a single chain polypeptide, and activate the alternative pathway. Upon activation of the alternative pathway, Factor B is cleaved by complement factor D yielding the noncatalytic chain Ba and the catalytic subunit Bb. The active subunit Bb is a serine protease that associates with C3b to form the alternative pathway C3 convertase (i.e., C3bBb complex). In some embodiments, the anti-Factor B antibody of the present disclosure also binds to Factor Bb. Factor Bb is involved in the proliferation of preactivated B lymphocytes, while Ba inhibits their proliferation.

In some embodiments, the anti-Factor B antibody binds to a Factor Bb portion and inhibits dissociation of a C3bBb complex. In certain embodiments, the anti-Factor B antibody inhibits dissociation of the C3bBb complex into a Factor Bb and a C3b. In some embodiments, the anti-Factor B antibody is a bispecific antibody or a multispecific antibody.

In certain embodiments, the anti-Factor B antibody specifically binds to Factor Bb. In some embodiments, the anti-Factor B specifically binds to both Factor Bb and Factor B. In some embodiments, the anti-Factor B antibody specifically binds to a C3bBb complex. In some embodiments, the anti-Factor B antibody reduces, inhibits, or prevents degradation of a C3bBb complex. In some embodiments, the anti-Factor B antibody induces C3 cleavage in serum. In some embodiments, the anti-Factor B antibody reduces serum concentration of C3. In some embodiments, the anti-Factor B antibody induces accumulation of C3b on the surface of the cell. In some embodiments, the anti-Factor B antibody induces membrane attack deposition on the surface of the cell.

In some embodiments, the anti-Factor B antibody binds Factor Bb of the C3bBb complex. In some embodiments, the anti-Factor B antibody binds Factor B prior to Factor B binding to $C3(H_2O)$ or C3b. In other embodiments, the anti-Factor B antibody binds Factor B following Factor B binding to $C3(H_2O)$ or C3b and prior to Factor B cleavage by Factor D. In some embodiments, the anti-Factor B antibody binds Factor B and remains bound to Factor Bb following cleavage of Factor B by Factor D.

In certain embodiments, the anti-Factor B antibody diminishes the activity of a complement pathway. In some embodiments, the anti-Factor B antibody diminishes the activity of serum complement activity. In some embodiments, the anti-Factor B antibody diminishes the activity of an alternative complement pathway in serum. In some embodiments, the anti-Factor B antibody diminishes the activity of a classical complement pathway. In certain embodiments, the anti-Factor B antibody diminishes the activity of a complement pathway by promoting consumption of C3 until circulating levels of C3 no longer support complement pathway activation.

In some embodiments, the anti-Factor B antibody inhibits dissociation of a C3bBb complex, e.g., into a Factor Bb and a C3b, by reducing or blocking inhibitor-mediated dissociation of the C3bBb complex. In some embodiments, the anti-Factor B antibody reduces or blocks DAF/CD55 mediated dissociation of the C3bBb complex.

Complement decay-accelerating factor, also known as CD55 or DAF, is a protein that, in humans, is encoded by the CD55 gene. DAF regulates the complement system on the cell surface. It recognizes C4b and C3b fragments that are created during C4 (classical complement pathway and lectin pathway) and C3 (alternate complement pathway) activation. Interaction of DAF with cell-associated C4b of the classical and lectin pathways interferes with the conversion of C2 to C2a, thereby preventing formation of the C4b2a C3 convertase, and interaction of DAF with C3b of the alternative pathway interferes with the conversion of factor B to Bb by factor D, thereby preventing formation of the C3bBb complex of the alternative pathway. By reducing or blocking DAF/CD55 mediated dissociation of the C3bBb complex, the present methods using anti-Factor B antibody prevent negative regulation of a complement pathway, e.g., alternative pathway, thereby inducing complement activity.

In some embodiments, the anti-Factor B antibody reduces or blocks Factor H mediated dissociation of the C3bBb complex. In some embodiments, the anti-Factor B antibody reduces or blocks CR1 mediated dissociation of the C3bBb complex. In some embodiments, the anti-Factor B antibody reduces or blocks binding of an inhibitor to the C3bBb complex. In some embodiments, the inhibitor is selected from the group consisting of DAF/CD55, Factor H, CR1, and any combination thereof.

In some embodiments, the complement activity comprises complement-mediated cell death. In some embodiments, the complement activity induces cell death of the target cell. In some embodiments, the target cell death comprises phagocytosis of the target cell by a second cell, e.g., an immune cell. In some embodiments, the cell death occurs following formation of a terminal lytic complex (MAC; C5b-9) in the plasma membrane of the target cell. In some embodiments, the cell death comprises apoptosis of the target cell.

In some embodiments, the complement activity comprises production of an opsonin. An opsonin, as referenced herein, is a molecule that facilitates targeting of a cell for termination, e.g., phagocytosis, by an immune cell. In some embodiments, the opsonin comprises C3b, iC3b, or both C3b and iC3b. In some embodiments, the complement activity comprises production of an anaphylatoxin. In some embodiments, the anaphylatoxin comprises C3a, C5a, or both C3a and C5a. In some embodiments, the anaphylatoxin comprises a chemoattractant, which attracts immune cells to the target cell. In some embodiments, the complement activity comprises formation of a terminal lytic complex ("membrane attack complex" or "MAC;" C5b-9). In some embodiments, the terminal lytic complex forms in the plasma membrane of the target cell, creating a pore, which facilitates the death of the target cell.

In some embodiments, the target cell is an in vivo cell. In certain embodiments, the in vivo cell is an autologous cell, e.g., a human cell produced by the human in which it is located, e.g., a native cell. In other embodiments, the in vivo cell is a foreign cell, e.g., a pathogen. In some embodiments, the in vivo cell is an aberrant cell, e.g., a cancer cell or a hyperactive immune cell. In some embodiments, the in vivo cell is a cancer cell. In some embodiments, the cancer is selected from the group consisting of melanoma (MEL); renal cell carcinoma (RCC); lung cancer; colorectal cancer (CRC); prostate cancer; liver cancer; squamous cell carcinoma of the head and neck; carcinomas of the esophagus, ovary, gastrointestinal tract, and breast; a hematologic malignancy such as multiple myeloma, B-cell lymphoma, T-cell lymphoma, Hodgkin's lymphoma/primary mediastinal B-cell lymphoma, and chronic myelogenous leukemia; and any combination thereof. In other embodiments, the in vivo cell is a pathogen. In some embodiments, the in vivo cell is selected from the group consisting of a bacteria, a fungus, a parasite, and any combination thereof. In some embodiments, the in vivo cell is infected by a virus.

Induction of complement activity can be measured using any methods known in the art. In some embodiments, induction of complement activity is measured by detecting the level of C3b on a cell surface. In some embodiments, induction of complement activity is measured by detecting the level of C3a in patient serum. In some embodiments, induction of complement activity is measured by detecting the level of C3 in patient serum. In some embodiments, induction of complement activity is measured by detecting the level of Factor Ba in patient serum. In some embodiments, induction of complement activity is measured by detecting the level of C3bBb on a cell surface. In some embodiments, induction of complement activity is measured by detecting the level of target cell death. In some embodiments, induction of complement activity is measured by detecting the level of an immune response. In certain embodiments, the immune response is characterized by localization or one or more immune cells to the target cell.

In some embodiments, contacting a cell with the anti-Factor B antibody increases the level of C3b on the surface of a cell relative to the level of C3b prior to the contacting. In some embodiments, contacting a cell with the anti-Factor B antibody increases the level of C3b in the serum of a subject relative to the level of C3b prior to the contacting. In some embodiments, contacting a cell with the anti-Factor B antibody increases the level of C3a in the serum of a subject relative to the level of C3a prior to the contacting. In some embodiments, contacting a cell with the anti-Factor B antibody decreases the level of C3 in the serum of a subject relative to the level of C3 prior to the contacting. In some embodiments, contacting a cell with the anti-Factor B antibody increases the level of C3bBb on the surface of a cell relative to the level of C3bBb prior to the contacting.

In some embodiments, the anti-Factor B antibodies of the present disclosure inhibit dissociation of a C3bBb complex in the presence of an inhibitor of C3bBb, e.g., DAF/CD55 and/or Factor H. Without committing to a mechanism, by inhibiting a membrane bound inhibitor of the alternate pathway, the anti-Factor B antibodies induce C3b production on the surface of the cell and promote the alternative complement pathway.

Certain aspects of the present disclosure are directed to methods of inducing a complement activity on a surface of a cell in a subject in need thereof, comprising contacting the cell with an effective amount of an anti-Factor B antibody, wherein the anti-Factor B antibody inhibits dissociation of a C3bBb complex. In certain embodiments, the anti-Factor B antibody inhibits dissociation of the C3bBb complex into a Factor Bb and a C3b. In some embodiments, the subject is a human. In certain embodiments, the subject is afflicted by a disease or a condition.

In some other embodiments, the anti-Factor B antibody disclosed herein, when administered in vivo, does not increase a risk of infection, e.g., bacterial infection. In certain embodiments, the anti-Factor B antibody disclosed herein, when administered in vivo, does not increase a risk of infection compared to an anti-C5 antibody. In some embodiments, the infection is caused by *N. meningitidis* and *S. pneumoniae*. In other embodiments, the infection is associated with or causes meningitis.

In certain embodiments, the subject has a disease or condition comprising a cancer. The particular cancer can be selected from any cancer known in the art. In some embodiments, the cancer is selected from the group consisting of melanoma (MEL); renal cell carcinoma (RCC); lung cancer; colorectal cancer (CRC); prostate cancer; liver cancer; squamous cell carcinoma of the head and neck; carcinomas of the esophagus, ovary, gastrointestinal tract, and breast; a hematologic malignancy such as multiple myeloma, B-cell lymphoma, T-cell lymphoma, Hodgkin's lymphoma/primary mediastinal B-cell lymphoma, and chronic myelogenous leukemia; and any combination thereof. In certain embodiments, the subject has a hematologic malignancy. In certain embodiments, the subject has a B cell lymphoma. In other embodiments, the subject has a T-cell lymphoma. In other embodiments, the subject has leukemia, e.g., chronic myelogenous leukemia.

In certain embodiments, the subject has a disease or condition comprising an autoimmune disease. The particular autoimmune disease can be selected from any autoimmune disease known in the art. In some embodiments, the autoimmune disease is selected from the group consisting of multiple sclerosis, type 1 diabetes, rheumatoid arthritis, lupus, celiac disease, Sjorgren's syndrome, polymyalgia, ankylosing spondylitis, alopecia areata, vasculitis, temporal arteritis, and any combination thereof. In certain embodiments, the subject multiple sclerosis. In other embodiments, the subject has diabetes, e.g., type 1 diabetes. In other embodiments, the subject has rheumatoid arthritis. In other embodiments, the subject has lupus. In other embodiments, the subject has celiac disease.

Autoimmune diseases or disorders that can be treated using a method of the present disclosure are, but are not limited to, Addison's disease, age-related macular degeneration, alopecia, autoimmune hepatitis (e.g., autoimmune hepatitis associated with hepatitis B virus infection; autoimmune hepatitis associated with hepatitis C virus infection), autoimmune hemolytic anemia, autoimmune skin diseases, autoimmune thyroid disease, bullous pemphigoid, celiac disease, cold agglutinin disease, dermatomyositis, type 1 diabetes mellitus, Grave's disease, Goodpasture's syndrome, Hashimoto's disease, hypoparathyroidism, hypopituitarism, hypothyroidism, idiopathic thrombocytopenic purpura, inflammatory bowel disease (e.g., Crohn's disease; ulcerative colitis), multiple sclerosis, myasthenia gravis, myocarditis, neuromyelitis optica, pemphigus vulgaris, pemphigus foliaceus, polymyositis, psoriasis, rheumatoid arthritis, sarcoidosis, scleroderma, Sjogren's syndrome, systemic lupus erythematosus, uveitis, and Wegener's granulomatosis and poly/dermatomyositis.

Diseases that can be treated using a method of the present disclosure include, e.g., age-related autoimmune disorders, age-related macular degeneration, Alzheimer's disease, amyotrophic lateral sclerosis, anaphylaxis, argyrophilic grain dementia, arthritis (e.g., rheumatoid arthritis), asthma, atherosclerosis, atypical hemolytic uremic syndrome, autoimmune diseases, autoimmune hemolytic anemia, Barraquer-Simons syndrome, Behcet's disease, British type amyloid angiopathy, bullous pemphigoid, Buerger's disease, C1q nephropathy, cancer, catastrophic antiphospholipid syndrome, cerebral amyloid angiopathy, cold agglutinin disease, corticobasal degeneration, Creutzfeldt-Jakob disease, Crohn's disease, cryoglobulinemic vasculitis, dementia pugilistica, dementia with Lewy Bodies (DLB), diffuse neurofibrillary tangles with calcification, Discoid lupus erythematosus, Down's syndrome, focal segmental glomerulosclerosis, formal thought disorder, frontotemporal dementia (FTD), frontotemporal dementia with parkinsonism linked to chromosome 17, frontotemporal lobar degeneration, Gerstmann-Straussler-Scheinker disease, Guillain-Barre syndrome, Hallervorden-Spatz disease, hemolytic-uremic syndrome, hereditary angioedema, hypophosphastasis, idiopathic pneumonia syndrome, immune complex diseases, inclusion body myositis, infectious disease (e.g., disease caused by bacterial (e.g., *Neisseria meningitidis* or *Streptococcus*) viral (e.g., human immunodeficiency virus (HIV)), or other infectious agents), inflammatory disease, ischemia/reperfusion injury, mild cognitive impairment, immunothrombocytopenic purpura (ITP), molybdenum cofactor deficiency (MoCD) type A, membranoproliferative glomerulonephritis (MPGN) I, membranoproliferative glomerulonephritis (MPGN) II (dense deposit disease), membranous nephritis, multi-infarct dementia, lupus (e.g., systemic lupus erythematosus (SLE)), glomerulonephritis, Kawasaki disease, multifocal motor neuropathy, multiple sclerosis, multiple system atrophy, myasthenia gravis, myocardial infarction, myotonic dystrophy, neuromyelitis optica, Niemann-Pick disease type C, non-Guamanian motor neuron disease with neurofibrillary tangles, Parkinson's disease, Parkinson's disease with dementia, paroxysmal nocturnal hemoglobinuria, Pemphigus vulgaris, Pick's disease, postencephalitic parkinsonism, polymyositis, prion protein cerebral amyloid angiopathy, progressive subcortical gliosis, progressive supranuclear palsy, psoriasis, sepsis, Shiga-toxin *E coli* (STEC)-HuS, spinal muscular atrophy, stroke, subacute sclerosing panencephalitis, Tangle only dementia, transplant rejection, vasculitis (e.g., ANCA associated vasculitis), Wegner's granulomatosis, sickle cell disease, cryoglobulinemia, mixed cryoglobulinemia, essential mixed cryoglobulinemia, Type II mixed cryoglobulinemia, Type III mixed cryoglobulinemia, nephritis, drug-induced thrombocytopenia, lupus nephritis, bullous pemphigoid, Epidermolysis bullosa acquisita, delayed hemolytic transfusion reaction, hypocomplementemic urticarial vasculitis syndrome, pseudophakic bullous keratopathy, and platelet refractoriness.

In certain embodiments, the subject has an infection. In some embodiments, the infection is selected from the group consisting of a bacterial infection, a viral infection, a fungal infection, a parasitic infection, or any combination thereof.

In certain embodiments, the anti-Factor B antibody treats a disease or condition by inducing cell death. In some embodiments, the anti-Factor B antibody induces cell death by facilitating a targeted immune response, e.g., by increasing the level of an opsonin or an anaphylatoxin, against one or more cells of the disease or condition.

The anti-Factor B antibodies disclosed herein can be administered by any means known in the art. In some embodiments, the anti-Factor B antibodies are administered parenterally, intravenously, subcutaneously, intradermally, transdermally, intramuscularly, orally, intraocularly, intrathecally, intraperitoneally, intranasally, buccally, sublingually, rectally, vaginally, or via pulmonary route. In certain embodiments, the anti-Factor B antibodies are administered intravenously. In certain embodiments, the anti-Factor B antibodies are administered subcutaneously.

II.A. Anti-Factor B Antibodies

In some aspects of the present disclosure, the anti-Factor B antibody specifically binds Factor Bb, e.g., human Factor Bb (Table 1; SEQ ID NO: 15). In some aspects, the anti-Factor B antibody specifically binds Factor B, e.g., human Factor B, in addition to Factor Bb. In some aspects, the anti-Factor B antibody specifically binds the C3bBb complex via Factor Bb.

In particular embodiments, the anti-Factor B antibody competes for binding to Factor Bb, e.g., of the C3bBb complex, with a reference antibody, wherein the reference antibody comprises a heavy chain and a light chain; wherein the heavy chain comprises a heavy chain variable (VH) region, and the light chain comprises a light chain variable (VL) region; wherein the VH region comprises a VH complementarity determining region 1 (CDR1), a VH CDR2, and a VH CDR3; wherein the VL region comprises a VL CDR1, a VL CDR2, and a VL CDR3; wherein the VH CDR1 comprises SEQ ID NO: 1, the VH CDR2 comprises SEQ ID NO: 2, and the VH CDR3 comprises SEQ ID NO: 3; and wherein the VL CDR1 comprises SEQ ID NO: 4, the VL CDR2 comprises SEQ ID NO: 5, and the VL CDR3 comprises SEQ ID NO: 6 (Table 2).

TABLE 2

Anti-Factor B Antibody Sequences

| | Amino Acid Sequence | Nucleotide Sequence |
|---|---|---|
| VH CDR1 | GYSFTDYL (SEQ ID NO: 1) | |

TABLE 2-continued

Anti-Factor B Antibody Sequences

| | Amino Acid Sequence | Nucleotide Sequence |
|---|---|---|
| VH CDR2 | INPYNGDA (SEQ ID NO: 2) | |
| VH CDR3 | ARLENDYGFTY (SEQ ID NO: 3) | |
| VH | EVQLQQSGPELVKPGASVKMSCKASGYSF TDYLMNWVKQSHGKSLEWIGRINPYNGDA FYNQRFKGKATLTVDKSSSTAHMELRSLT SEDSALYYCARLENDYGFTYWGQGTLVTV SA (SEQ ID NO: 7) | GAAGTGCAACTCCAACAGAGCGGACCAGAACTTG TGAAGCCCGGAGCCTCAGTGAAGATGTCCTGTAA GGCTTCCGGATATTCCTTCACTGATTACCTGATG AACTGGGTCAAGCAGAGCCATGGAAAGTCCCTGG AGTGGATTGGGCGCATCAATCCGTACAACGGCGA TGCGTTCTACAACCAGCGGTTTAAGGGGAAGGCC ACCCTGACCGTGGACAAGTCATCGTCCACCGCCC ACATGGAGTTGAGATCCCTGACCTCGGAGGACAG CGCCCTCTACTACTGCGCAAGGCTGGAAAACGAT TACGGCTTCACCTACTGGGGCCAGGGTACTCTGG TCACTGTGTCCGCT (SEQ ID NO: 11) |
| Heavy Chain | EVQLQQSGPELVKPGASVKMSCKASGYSF TDYLMNWVKQSHGKSLEWIGRINPYNGDA FYNQRFKGKATLTVDKSSSTAHMELRSLT SEDSALYYCARLENDYGFTYWGQGTLVTV SASTKGPSVFPLAPCSRSTSESTAALGCL VKDYFPEPVTVSWNSGALTSGVHTFPAVL QSSGLYSLSSVVTVPSSSLGTKTYTCNVD HKPSNTKVDKRVESKYGPPCPPCPAPEFE GGPSVFLFPPKPKDTLMISRTPEVTCVVV DVSQEDPEVQFNWYVDGVEVHNAKTKPRE EQFNSTYRVVSVLTVLHQDWLNGKEYKCK VSNKGLPSSIEKTISKAKGQPREPQVYTL PPSQEEMTKNQVSLTCLVKGFYPSDIAVE WESNGQPENNYKTTPPVLDSDGSFFLYSR LTVDKSRWQEGNVFSCSVMHEALHNHYTQ KSLSLSLGK (SEQ ID NO: 9) | GAAGTGCAACTCCAACAGAGCGGACCAGAACTTG TGAAGCCCGGAGCCTCAGTGAAGATGTCCTGTAA GGCTTCCGGATATTCCTTCACTGATTACCTGATG AACTGGGTCAAGCAGAGCCATGGAAAGTCCCTGG AGTGGATTGGGCGCATCAATCCGTACAACGGCGA TGCGTTCTACAACCAGCGGTTTAAGGGGAAGGCC ACCCTGACCGTGGACAAGTCATCGTCCACCGCCC ACATGGAGTTGAGATCCCTGACCTCGGAGGACAG CGCCCTCTACTACTGCGCAAGGCTGGAAAACGAT TACGGCTTCACCTACTGGGGCCAGGGTACTCTGG TCACTGTGTCCGCTTCCACCAAGGGCCCATCCGT CTTCCCCCTGGCGCCCTGCTCCAGGAGCACCTCC GAGAGCACAGCCGCCCTGGGCTGCCTGGTCAAGG ACTACTTCCCCGAACCGGTGACGGTGTCGTGGAA CTCAGGCGCCCTGACCAGCGGCGTGCACACCTTC CCGGCTGTCCTACAGTCCTCAGGACTCTACTCCC TCAGCAGCGTGGTGACCGTGCCCTCCAGCAGCTT GGGCACGAAGACCTACACCTGCAATGTAGATCAC AAGCCCAGCAACACCAAGGTGGACAAGAGAGTTG AGTCCAAATATGGTCCCCCATGCCCACCATGCCC AGCACCTGAGTTCGAGGGGGGACCATCAGTCTTC CTGTTCCCCCCAAAACCCAAGGACACTCTCATGA TCTCCCGGACCCCTGAGGTCACGTGCGTGGTGGT GGACGTGAGCCAGGAAGACCCCGAGGTCCAGTTC AACTGGTACGTGGATGGCGTGGAGGTGCATAATG CCAAGACAAAGCCGCGGGAGGAGCAGTTCAACAG CACGTACCGTGTGGTCAGCGTCCTCACCGTCCTG CACCAGGACTGGCTGAACGGCAAGGAGTACAAGT GCAAGGTCTCCAACAAAGGCCTCCCGTCCTCCAT CGAGAAAACCATCTCCAAAGCCAAAGGGCAGCCC CGAGAGCCACAGGTGTACACCCTGCCCCCATCCC AGGAGGAGATGACCAAGAACCAGGTCAGCCTGAC CTGCCTGGTCAAAGGCTTCTACCCCAGCGACATC GCCGTGGAGTGGGAGAGCAATGGGCAGCCGGAGA ACAACTACAAGACCACGCCTCCCGTGCTGGACTC CGACGGCTCCTTCTTCCTCTACAGCAGGCTAACC GTGGACAAGAGCAGGTGGCAGGAGGGGAATGTCT TCTCATGCTCCGTGATGCATGAGGCTCTGCACAA CCACTACACACAGAAGAGCCTCTCCCTGTCTCTG GGTAAATGA (SEQ ID NO: 12) |
| VL CDR1 | KSLLHSNGITY (SEQ ID NO: 4) | |
| VL CDR2 | RMS (SEQ ID NO: 5) | |
| VL CDR3 | AQMLERPWT (SEQ ID NO: 6) | |
| VL | DIVMTQAAFSNPVTLGTSASISCSSSKSL LHSNGITYLYWYLQRPGQSPQLLIYRMSN LASGVPDRFSGSGSGTDFTLRISRVEAED VGVYYCAQMLERPWTFGGGTKLEIK (SEQ ID NO: 8) | GATATCGTGATGACCCAGGCTGCCTTCTCCAACC CTGTGACTCTCGGAACCTCCGCCTCAATCTCCTG CTCGTCATCCAAGTCCCTGCTTCACTCGAACGGG ATTACCTACCTGTATTGGTACTTGCAAAGACCGG GCCAGAGCCCCCAGCTGCTGATCTACCGCATGTC GAACCTGGCCAGCGGAGTGCCAGACCGGTTCTCC GGTTCTGGTTCCGGGACTGACTTCACTCTCGCGG ATTAGCAGGGTGGAAGCAGAGGACGTCGGAGTGTA |

TABLE 2-continued

Anti-Factor B Antibody Sequences

| | Amino Acid Sequence | Nucleotide Sequence |
|---|---|---|
| | | CTACTGTGCGCAGATGCTCGAGCGCCCGTGGACC TTTGGCGGAGGCACCAAGCTGGAAATCAAGACT (SEQ ID NO: 13) |
| Light Chain | DIVMTQAAFSNPVTLGTSASISCSSSKSL LHSNGITYLYWYLQRPGQSPQLLIYRMSN LASGVPDRFSGSGSGTDFTLRISRVEAED VGVYYCAQMLERPWTFGGGTKLEIKTVAA PSVFIFPPSDEQLKSGTASVVCLLNNFYP REAKVQWKVDNALQSGNSQESVTEQDSKD STYSLSSTLTLSKADYEKHKVYACEVTHQ GLSSPVTKSFNRG (SEQ ID NO: 10) | GATATCGTGATGACCCAGGCTGCCTTCTCCAACC CTGTGACTCTCGGAACCTCCGCCTCAATCTCCTG CTCGTCATCCAAGTCCCTGCTTCACTCGAACGGG ATTACCTACCTGTATTGGTACTTGCAAAGACCGG GCCAGAGCCCCCAGCTGCTGATCTACCGCATGTC GAACCTGGCCAGCGGAGTGCCAGACCGGTTCTCC GGTTCTGGTTCCGGGACTGACTTCACTCTGCGGA TTAGCAGGGTGGAAGCAGAGGACGTCGGAGTGTA CTACTGTGCGCAGATGCTCGAGCGCCCGTGGACC TTTGGCGGAGGCACCAAGCTGGAAATCAAGACTG TGGCTGCACCATCTGTCTTCATCTTCCCGCCATC TGATGAGCAGTTGAAATCTGGAACTGCCTCTGTT GTGTGCCTGCTGAATAACTTCTATCCCAGAGAGG CCAAAGTACAGTGGAAGGTGGATAACGCCCTCCA ATCGGGTAACTCCCAGGAGAGTGTCACAGAGCAG GACAGCAAGGACAGCACCTACAGCCTCAGCAGCA CCCTGACGCTGAGCAAAGCAGACTACGAGAAACA CAAAGTCTACGCCTGCGAAGTCACCCATCAGGGC CTGAGCTCGCCCGTCACAAAGAGCTTCAACAGGG GAGAGTGTTAG (SEQ ID NO: 14) |

In some embodiments, the anti-Factor B antibody competes for binding to Factor Bb, e.g., of the C3bBb complex, with a reference antibody, wherein the reference antibody comprises a heavy chain variable region comprising SEQ ID NO: 7 and a light chain variable region comprising SEQ ID NO: 8.

In some embodiments, the anti-Factor B antibody binds the same epitope on Factor Bb, e.g., of the C3bBb complex, as a reference antibody, wherein the reference antibody comprises a heavy chain and a light chain; wherein the heavy chain comprises a VH region, and the light chain comprises a VL region; wherein the VH region comprises a VH CDR1, a VH CDR2, and a VH CDR3; wherein the VL region comprises a VL CDR1, a VL CDR2, and a VL CDR3; wherein the VH CDR1 comprises SEQ ID NO: 1, the VH CDR2 comprises SEQ ID NO: 2, and the VH CDR3 comprises SEQ ID NO: 3; and wherein the VL CDR1 comprises SEQ ID NO: 4, the VL CDR2 comprises SEQ ID NO: 5, and the VL CDR3 comprises SEQ ID NO: 6.

In some embodiments, the anti-Factor B antibody binds the same epitope on Factor Bb, e.g., of the C3bBb complex, as a reference antibody, wherein the reference antibody comprises a heavy chain variable region comprising SEQ ID NO: 7 and a light chain variable region comprising SEQ ID NO: 8.

In some embodiments, the anti-Factor B antibody comprises a heavy chain and a light chain; wherein the heavy chain comprises a VH region, and the light chain comprises a VL region; wherein the VH region comprises a VH CDR1, a VH CDR2, and a VH CDR3; wherein the VL region comprises a VL CDR1, a VL CDR2, and a VL CDR3; and wherein the VH CDR3 comprises SEQ ID NO: 3 or SEQ ID NO: 3 with one or two amino acid substitutions.

In some embodiments, the anti-Factor B antibody comprises a heavy chain and a light chain; wherein the heavy chain comprises a VH region, and the light chain comprises a VL region; wherein the VH region comprises a VH CDR1, a VH CDR2, and a VH CDR3; wherein the VL region comprises a VL CDR1, a VL CDR2, and a VL CDR3; and wherein the VH CDR1 comprises SEQ ID NO: 1 or SEQ ID NO: 1 with one or two amino acid substitutions.

In some embodiments, the anti-Factor B antibody comprises a heavy chain and a light chain; wherein the heavy chain comprises a VH region, and the light chain comprises a VL region; wherein the VH region comprises a VH CDR1, a VH CDR2, and a VH CDR3; wherein the VL region comprises a VL CDR1, a VL CDR2, and a VL CDR3; and wherein the VH CDR2 comprises SEQ ID NO: 2 or SEQ ID NO: 2 with one or two amino acid substitutions.

In some embodiments, the anti-Factor B antibody comprises a heavy chain and a light chain; wherein the heavy chain comprises a VH region, and the light chain comprises a VL region; wherein the VH region comprises a VH CDR1, a VH CDR2, and a VH CDR3; wherein the VL region comprises a VL CDR1, a VL CDR2, and a VL CDR3; and wherein the VH CDR1 comprises SEQ ID NO: 4 or SEQ ID NO: 4 with one or two amino acid substitutions.

In some embodiments, the anti-Factor B antibody comprises a heavy chain and a light chain; wherein the heavy chain comprises a VH region, and the light chain comprises a VL region; wherein the VH region comprises a VH CDR1, a VH CDR2, and a VH CDR3; wherein the VL region comprises a VL CDR1, a VL CDR2, and a VL CDR3; and wherein the VH CDR2 comprises SEQ ID NO: 5 or SEQ ID NO: 5 with one or two amino acid substitutions.

In some embodiments, the anti-Factor B antibody comprises a heavy chain and a light chain; wherein the heavy chain comprises a VH region, and the light chain comprises a VL region; wherein the VH region comprises a VH CDR1, a VH CDR2, and a VH CDR3; wherein the VL region comprises a VL CDR1, a VL CDR2, and a VL CDR3; and wherein the VH CDR3 comprises SEQ ID NO: 6 or SEQ ID NO: 6 with one or two amino acid substitutions.

In particular embodiments, the anti-Factor B comprises a heavy chain and a light chain; wherein the heavy chain comprises a VH region, and the light chain comprises a VL region; wherein the VH region comprises a VH CDR1, a VH CDR2, and a VH CDR3; wherein the VL region comprises a VL CDR1, a VL CDR2, and a VL CDR3; wherein the VH CDR1 comprises SEQ ID NO: 1, the VH CDR2 comprises SEQ ID NO: 2, and the VH CDR3 comprises SEQ ID NO: 3; and wherein the VL CDR1 comprises SEQ ID NO: 4, the VL CDR2 comprises SEQ ID NO: 5, and the VL CDR3 comprises SEQ ID NO: 6.

In some embodiments, the VH of the anti-Factor B antibody comprises an amino acid sequence that is at least about 70%, at least about 75%, at least about 80%, at least about 85%, at least about 90%, at least about 95%, at least about 96%, at least about 97%, at least about 98%, or at least about 99% identical to SEQ ID NO: 7. In certain embodiments, the VH of the anti-Factor B antibody comprises SEQ ID NO: 7.

In some embodiments, the VL of the anti-Factor B antibody comprises an amino acid sequence that is at least 70%, at least about 75%, at least about 80%, at least about 85%, at least about 90%, at least about 95%, at least about 96%, at least about 97%, at least about 98%, or at least about 99% identical to SEQ ID NO: 8. In certain embodiments, the VL of the anti-Factor B antibody comprises SEQ ID NO: 8.

In some embodiments, the anti-Factor B antibody comprises a heavy chain comprising an amino acid sequence that is at least about 70%, at least about 75%, at least about 80%, at least about 85%, at least about 90%, at least about 95%, at least about 96%, at least about 97%, at least about 98%, or at least about 99% identical to SEQ ID NO: 9. In some embodiments, the anti-Factor B antibody comprises a heavy chain comprising SEQ ID NO: 9.

In some embodiments, the anti-Factor B antibody comprises a light chain comprising an amino acid sequence that is at least about 70%, at least about 75%, at least about 80%, at least about 85%, at least about 90%, at least about 95%, at least about 96%, at least about 97%, at least about 98%, or at least about 99% identical to SEQ ID NO: 10. In some embodiments, the anti-Factor B antibody comprises a light chain comprising SEQ ID NO: 10.

In some embodiments, the anti-Factor B antibody is a chimeric antibody. In certain embodiments, the anti-Factor B antibody is a humanized antibody. In particular embodiments, the anti-Factor B antibody is a human antibody. In certain embodiments, the anti-Factor B antibody is a bispecific antibody, wherein the bispecific antibody further comprises an antigen binding domain that is tissue or cell specific. In some embodiments, the anti-Factor B antibody is a multispecific antibody, wherein the multispecific antibody further comprises at least one antigen binding domain that is tissue or cell specific.

III. Bispecific and Multispecific Anti-Factor B Antibodies

Certain aspects of the present disclosure are directed to bispecific antibodies comprising (i) an anti-Factor B binding domain and (ii) a second antigen binding domain. In some embodiments, the anti-Factor B binding domain inhibits dissociation of a C3bBb complex. In certain embodiments, the bispecific antibody inhibits dissociation of the C3bBb complex into a Factor Bb and a C3b. In some embodiments, the second antigen binding domain is tissue specific or cell specific.

Other aspects of the present disclosure are directed to multispecific antibodies comprising (i) an anti-Factor B binding domain, (ii) a second antigen binding domain, and (iii) a third antigen binding domain. In some embodiments, the anti-Factor B binding domain inhibits dissociation of a C3bBb complex. In certain embodiments, the anti-Factor B binding domain inhibits dissociation of the C3bBb complex into a Factor Bb and a C3b. In some embodiments, the second antigen binding domain is tissue specific or cell specific. In some embodiments, the third antigen binding domain is tissue specific or cell specific. In particular embodiments, the multispecific antibody further comprises a fourth antigen binding domain, a fifth antigen binding domain, a sixth antigen binding domain, a seventh antigen binding domain, or more.

In some embodiments, the bispecific or multispecific antibody, e.g., the Factor Bb binding domain thereof, reduces, inhibits, or prevents degradation of a C3bBb complex. In some embodiments, the bispecific or multispecific antibody, e.g., the Factor Bb binding domain thereof, induces C3 cleavage in serum. In some embodiments, the bispecific or multispecific antibody, e.g., the Factor Bb binding domain thereof, reduces serum concentration of C3. In some embodiments, the bispecific or multispecific antibody, e.g., the Factor Bb binding domain thereof, induces accumulation of C3b on the surface of the cell. In some embodiments, the bispecific or multispecific antibody, e.g., the Factor Bb binding domain thereof, induces the loss of serum complement activity. In some embodiments, the bispecific or multispecific antibody, e.g., the Factor Bb binding domain thereof, induces membrane attack deposition on the surface of the cell.

In some embodiments, the bispecific or multispecific antibody, e.g., the Factor Bb binding domain thereof, specifically binds to a Factor Bb, e.g., of a C3bBb complex. In some embodiments, the bispecific or multispecific antibody, e.g., the Factor Bb binding domain thereof, binds Factor B prior to Factor B binding to $C3(H_2O)$ or C3b. In other embodiments, the bispecific or multispecific antibody, e.g., the Factor Bb binding domain thereof, binds Factor B following Factor B binding to $C3(H_2O)$ or C3b and prior to Factor B cleavage by Factor D. In some embodiments, the bispecific or multispecific antibody, e.g., the Factor Bb binding domain thereof, binds Factor B and remains bound to Factor Bb following cleavage of Factor B by Factor D.

In certain embodiments, the bispecific or multispecific antibody diminishes the activity of a complement pathway. In some embodiments, the bispecific or multispecific antibody diminishes the activity of serum complement activity. In some embodiments, the bispecific or multispecific antibody diminishes the activity of an alternative complement pathway in serum. In some embodiments, the bispecific or multispecific antibody diminishes the activity of a classical complement pathway. In certain embodiments, the bispecific or multispecific antibody diminishes the activity of a complement pathway by promoting consumption of C3 until circulating levels of C3 no longer support complement pathway activation.

In some embodiments, the bispecific or multispecific antibody, e.g., the Factor Bb binding domain thereof, inhibits dissociation of a C3bBb complex, e.g., into a Factor Bb and a C3b, by reducing or blocking inhibitor-mediated dissociation of the C3bBb complex. In some embodiments, the bispecific or multispecific antibody, e.g., the Factor Bb binding domain thereof, reduces or blocks DAF/CD55-mediated dissociation of the C3bBb complex. In some embodiments, the bispecific or multispecific antibody, e.g., the Factor Bb binding domain thereof, reduces or blocks Factor H-mediated dissociation of the C3bBb complex. In some embodiments, the bispecific or multispecific antibody, e.g., the Factor Bb binding domain thereof, reduces or blocks CR1-mediated dissociation of the C3bBb complex. In some embodiments, the bispecific or multispecific antibody, e.g., the Factor Bb binding domain thereof, reduces or blocks binding of an inhibitor to the C3bBb complex. In some embodiments, the inhibitor is selected from the group consisting of DAF/CD55, Factor H, CR1, and any combination thereof.

III.A. Antigen Binding Domains

In certain embodiments, the anti-Factor B binding domain competes for binding to Factor B and/or Factor Bb, e.g., of the C3bBb complex, with a reference antibody, wherein the reference antibody comprises a VH region and a VL region; wherein the VH region comprises a VH CDR1 comprising SEQ ID NO: 1, a VH CDR2 comprising SEQ ID NO: 2, and a VH CDR3 comprising SEQ ID NO: 3; and wherein the VL region comprises a VL CDR1 comprising SEQ ID NO: 4, the VL CDR2 comprising SEQ ID NO: 5, and a VL CDR3 comprising SEQ ID NO: 6.

In some embodiments, the anti-Factor B binding domain competes for binding to Factor Bb, e.g., of the C3bBb complex, with a reference antibody, wherein the reference antibody comprises a heavy chain variable region comprising SEQ ID NO: 7 and a light chain variable region comprising SEQ ID NO: 8.

In some embodiments, the anti-Factor B binding domain binds the same epitope on Factor Bb, e.g., of the C3bBb complex, as a reference antibody, wherein the reference antibody comprises a VH region and a VL region; wherein the VH region comprises a VH CDR1 comprising SEQ ID NO: 1, a VH CDR2 comprising SEQ ID NO: 2, and a VH CDR3 comprising SEQ ID NO: 3; and wherein the VL region comprises a VL CDR1 comprising SEQ ID NO: 4, the VL CDR2 comprising SEQ ID NO: 5, and a VL CDR3 comprising SEQ ID NO: 6.

In some embodiments, the anti-Factor B antibody binds the same epitope on Factor Bb, e.g., of the C3bBb complex, as a reference antibody, wherein the reference antibody comprises a heavy chain variable region comprising SEQ ID NO: 7 and a light chain variable region comprising SEQ ID NO: 8.

In some embodiments, the anti-Factor B binding domain comprises a heavy chain and a light chain; wherein the heavy chain comprises a VH region, and the light chain comprises a VL region; wherein the VH region comprises a VH CDR1, a VH CDR2, and a VH CDR3; wherein the VL region comprises a VL CDR1, a VL CDR2, and a VL CDR3; and wherein the VH CDR3 comprises SEQ ID NO: 3 or SEQ ID NO: 3 with one or two amino acid substitutions.

In some embodiments, the anti-Factor B binding domain comprises a VH region and a VL region; wherein the VH region comprises a VH CDR1, a VH CDR2, and a VH CDR3; wherein the VL region comprises a VL CDR1, a VL CDR2, and a VL CDR3; and wherein the VH CDR1 comprises SEQ ID NO: 1 or SEQ ID NO: 1 with one or two amino acid substitutions.

In some embodiments, the anti-Factor B binding domain comprises a VH region and a VL region; wherein the VH region comprises a VH CDR1, a VH CDR2, and a VH CDR3; wherein the VL region comprises a VL CDR1, a VL CDR2, and a VL CDR3; and wherein the VH CDR2 comprises SEQ ID NO: 2 or SEQ ID NO: 2 with one or two amino acid substitutions.

In some embodiments, the anti-Factor B binding domain comprises a VH region and a VL region; wherein the VH region comprises a VH CDR1, a VH CDR2, and a VH CDR3; wherein the VL region comprises a VL CDR1, a VL CDR2, and a VL CDR3; and wherein the VH CDR1 comprises SEQ ID NO: 4 or SEQ ID NO: 4 with one or two amino acid substitutions.

In some embodiments, the anti-Factor B binding domain comprises a VH region and a VL region; wherein the VH region comprises a VH CDR1, a VH CDR2, and a VH CDR3; wherein the VL region comprises a VL CDR1, a VL CDR2, and a VL CDR3; and wherein the VH CDR2 comprises SEQ ID NO: 5 or SEQ ID NO: 5 with one or two amino acid substitutions.

In some embodiments, the anti-Factor B binding domain comprises a VH region and a VL region; wherein the VH region comprises a VH CDR1, a VH CDR2, and a VH CDR3; wherein the VL region comprises a VL CDR1, a VL CDR2, and a VL CDR3; and wherein the VH CDR3 comprises SEQ ID NO: 6 or SEQ ID NO: 6 with one or two amino acid substitutions.

In particular embodiments, the anti-Factor B binding domain comprises a VH region and a VL region; wherein the VH region comprises a VH CDR1, a VH CDR2, and a VH CDR3; wherein the VL region comprises a VL CDR1, a VL CDR2, and a VL CDR3; wherein the VH CDR1 comprises SEQ ID NO: 1, the VH CDR2 comprises SEQ ID NO: 2, and the VH CDR3 comprises SEQ ID NO: 3; and wherein the VL CDR1 comprises SEQ ID NO: 4, the VL CDR2 comprises SEQ ID NO: 5, and the VL CDR3 comprises SEQ ID NO: 6.

In some embodiments, the VH of the anti-Factor B binding domain comprises an amino acid sequence that is at least about 70%, at least about 75%, at least about 80%, at least about 85%, at least about 90%, at least about 95%, at least about 96%, at least about 97%, at least about 98%, or at least about 99% identical to SEQ ID NO: 7. In certain embodiments, the VH of the anti-Factor B binding domain comprises SEQ ID NO: 7.

In some embodiments, the VL of the anti-Factor B binding domain comprises an amino acid sequence that is at least 70%, at least about 75%, at least about 80%, at least about 85%, at least about 90%, at least about 95%, at least about 96%, at least about 97%, at least about 98%, or at least about 99% identical to SEQ ID NO: 8. In certain embodiments, the VL of the anti-Factor B binding domain comprises SEQ ID NO: 8.

The second antigen binding and/or the third antigen binding domains can be selected to target any antigen that is expressed on the surface of a target cell. In some embodiments, the second antigen binding domain or the third antigen binding domain binds a tumor antigen. In some embodiments, the tumor antigen is selected from the group consisting of alphafetoprotein (AFP), carcinoembryonic antigen (CEA), CA-125, mucin 1 (MUC-1), epithelial tumor antigen (ETA), melanoma-associated antigen (MAGE), p53, an epidermal growth factor receptor (EGFR, e.g., HER1, ErbB-1, HER2, and/or EGFR12), CD30, and any combination thereof.

In other embodiments, the second antigen binding and/or the third antigen binding domains target any antigen that is expressed on the surface of a target cell except an endogenous BBB receptor and/or a transferrin receptor In some embodiments, the second antigen binding domain or the third antigen binding domain binds an antigen present on a B cell. In some embodiments, In some embodiments, the second antigen binding domain or the third antigen binding domain binds CD19. In some embodiments, the second antigen binding domain or the third antigen binding domain binds CD20. In other embodiments, the second antigen binding domain or the third antigen binding domain binds an antigen on the surface of autoantigen specific T effector cells. In some embodiments, the second antigen binding domain or the third antigen binding domain binds the voltage gated potassium channel Kv1.3.

In some embodiments, the bispecific antibody or the multispecific antibody is chimeric. In certain embodiments, the bispecific antibody or the multispecific antibody is humanized.

III.B. Methods

Certain aspects of the present disclosure are directed to methods of inducing a complement activity on a surface of a cell comprising contacting the cell with an effective amount of a bispecific antibody or a multispecific antibody disclosed herein. Other aspects of the present disclosure are directed to methods of inducing cell death in a subject in need thereof comprising administering an effective amount of a bispecific antibody or a multispecific antibody disclosed herein.

In some embodiments, the complement activity comprises complement-mediated cell death. In some embodiments, the complement activity induces cell death of the target cell. In some embodiments, the target cell death comprises phagocytosis of the target cell by a second cell, e.g., an immune cell. In some embodiments, the cell death occurs following formation of a terminal lytic complex (MAC; C5b-9) in the plasma membrane of the target cell. In some embodiments, the cell death comprises apoptosis of the target cell.

In some embodiments, the complement activity comprises production of an opsonin. In some embodiments, the opsonin comprises C3b, iC3b, or both C3b and iC3b. In some embodiments, the complement activity comprises production of an anaphylatoxin. In some embodiments, the anaphylatoxin comprises C3a, C5a, or both C3a and C5a. In some embodiments, the complement activity comprises formation of a terminal lytic complex (MAC; C5b-9). In some embodiments, the terminal lytic complex forms in the plasma membrane of the target cell, creating a pore, which facilitates the death of the target cell.

In some embodiments, the target cell is an in vivo cell. In certain embodiments, the in vivo cell is an autologous cell. In other embodiments, the in vivo cell is a foreign cell, e.g., a pathogen. In some embodiments, the in vivo cell is an aberrant cell. In some embodiments, the in vivo cell is a cancer cell. In some embodiments, the cancer is selected from the group consisting of melanoma (MEL); renal cell carcinoma (RCC); lung cancer; colorectal cancer (CRC); prostate cancer; liver cancer; squamous cell carcinoma of the head and neck; carcinomas of the esophagus, ovary, gastrointestinal tract, and breast; a hematologic malignancy such as multiple myeloma, B-cell lymphoma, T-cell lymphoma, Hodgkin's lymphoma/primary mediastinal B-cell lymphoma, and chronic myelogenous leukemia; and any combination thereof. In other embodiments, the in vivo cell is a pathogen. In some embodiments, the in vivo cell is selected from the group consisting of a bacteria, a fungus, a parasite, and any combination thereof. In some embodiments, the in vivo cell is infected by a virus.

In some embodiments, contacting a cell with the bispecific antibody or the multispecific antibody increases the level of C3b on the surface of a cell relative to the level of C3b prior to the contacting. In some embodiments, contacting a cell with the bispecific antibody or the multispecific antibody increases the level of C3b in the serum of a subject relative to the level of C3b prior to the contacting. In some embodiments, contacting a cell with the bispecific antibody or the multispecific antibody increases the level of C3a in the serum of a subject relative to the level of C3a prior to the contacting. In some embodiments, contacting a cell with the bispecific antibody or the multispecific antibody decreases the level of C3 in the serum of a subject relative to the level of C3 prior to the contacting. In some embodiments, contacting a cell with the bispecific antibody or the multispecific antibody increases the level of C3bBb on the surface of a cell relative to the level of C3bBb prior to the contacting.

Certain aspects of the present disclosure are directed to methods of inducing a complement activity on a surface of a cell in a subject in need thereof, comprising contacting the cell with an effective amount of a bispecific antibody or a multispecific antibody disclosed herein, wherein the bispecific antibody or the multispecific antibody inhibits dissociation of a C3bBb complex. In certain embodiments, the bispecific or multispecific antibody inhibits dissociation of the C3bBb complex into a Factor Bb and a C3b. In some embodiments, the subject is a human. In certain embodiments, the subject is afflicted by a disease or a condition.

Other aspects of the present disclosure are directed to methods of treating a disease or condition by inducing cell death in a subject in need thereof comprising administering an effective amount of a bispecific antibody or a multispecific antibody disclosed herein.

In certain embodiments, the subject has a disease or condition comprising a cancer. The particular cancer can be selected from any cancer known in the art. In some embodiments, the cancer is selected from the group consisting of melanoma (MEL); renal cell carcinoma (RCC); lung cancer; colorectal cancer (CRC); prostate cancer; liver cancer; squamous cell carcinoma of the head and neck; carcinomas of the esophagus, ovary, gastrointestinal tract, and breast; a hematologic malignancy such as multiple myeloma, B-cell lymphoma, T-cell lymphoma, Hodgkin's lymphoma/primary mediastinal B-cell lymphoma, and chronic myelogenous leukemia; and any combination thereof. In certain embodiments, the subject has a hematologic malignancy. In certain embodiments, the subject has a B cell lymphoma. In other embodiments, the subject has a T-cell lymphoma. In other embodiments, the subject has leukemia, e.g., chronic myelogenous leukemia.

In certain embodiments, the subject has a disease or condition comprising an autoimmune disease. The particular autoimmune disease can be selected from any autoimmune disease known in the art. In some embodiments, the autoimmune disease is selected from the group consisting of multiple sclerosis, type 1 diabetes, rheumatoid arthritis, lupus, celiac disease, Sjorgren's syndrome, polymyalgia, ankylosing spondylitis, alopecia areata, vasculitis, temporal arteritis, and any combination thereof. In certain embodiments, the subject multiple sclerosis. In other embodiments, the subject has diabetes, e.g., type 1 diabetes. In other embodiments, the subject has rheumatoid arthritis. In other embodiments, the subject has lupus. In other embodiments, the subject has celiac disease.

In certain embodiments, the subject has an infection. In some embodiments, the infection is selected from the group consisting of a bacterial infection, a viral infection, a fungal infection, a parasitic infection, or any combination thereof.

In certain embodiments, the bispecific antibody or the multispecific antibody treats a disease or condition by inducing cell death. In some embodiments, the bispecific antibody or the multispecific antibody induces cell death by facilitating a targeted immune response, e.g., by increasing the level of an opsonin or an anaphylatoxin, against one or more cells of the disease or condition. In some embodiments, the bispecific antibody or the multispecific antibody induces cell death by formation of a terminal lytic complex ("membrane attack complex" or "MAC;" C5b-9). In some embodiments, the terminal lytic complex forms in the plasma membrane of the target cell, creating a pore, which facilitates the death of the target cell.

The bispecific antibody or the multispecific antibody disclosed herein can be administered by any means known in the art. In some embodiments, the bispecific antibody or the multispecific antibody is administered parenterally, intravenously, subcutaneously, intradermally, transdermally, intramuscularly, orally, intraocularly, intrathecally, intraperitoneally, intranasally, buccally, sublingually, rectally, vaginally, or via pulmonary route. In certain embodiments, the bispecific antibody or the multispecific antibody is administered intravenously. In certain embodiments, the bispecific antibody or the multispecific antibody is administered subcutaneously.

IV. Polynucleotides

Certain aspects of the present disclosure are directed to a polynucleotide or set of polynucleotides comprising a nucleic acid encoding an antibody disclosed herein. In some embodiments, the polynucleotide comprises an nucleic acid sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO: 11. In certain embodiments, the polynucleotide comprises SEQ ID NO: 11.

In some embodiments, the polynucleotide comprises an nucleic acid sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO: 13. In certain embodiments, the polynucleotide comprises SEQ ID NO: 13.

In some embodiments, the polynucleotide comprises an nucleic acid sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO: 12. In certain embodiments, the polynucleotide comprises SEQ ID NO: 12.

In some embodiments, the polynucleotide comprises an nucleic acid sequence that is at least about 60%, at least about 65%, at least about 70%, at least about 75%, at least about 80%, at least about 85%, at least about 90%, at least about 95%, at least about 96%, at least about 97%, at least about 98%, or at least about 99% identical to SEQ ID NO: 13. In certain embodiments, the polynucleotide comprises SEQ ID NO: 13.

A nucleotide sequence encoding an antibody of the present disclosure can be operably linked to one or more regulatory elements, such as a promoter and enhancer, that allow expression of the nucleotide sequence in the intended target cells (e.g., a cell that is genetically modified to synthesize the encoded antibody). Thus, in some cases, the present disclosure provides a nucleic acid comprising a nucleotide sequence encoding an antibody of the present disclosure, where the nucleotide sequence is operably linked to one or more regulatory elements, e.g., a promoter and/or an enhancer.

Suitable promoter and enhancer elements are known in the art. Suitable promoters for use in prokaryotic host cells include, but are not limited to, a bacteriophage T7 RNA polymerase promoter; a T3 promoter; a T5 promoter; a lambda P promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; a gpt promoter; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to, Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding the operator), a tryptophan promoter operator (when complexed with tryptophan, TrpR repressor protein has a conformation that binds the operator; in the absence of tryptophan, the TrpR repressor protein has a conformation that does not bind the operator), and a tac promoter operator (see, for example, deBoer et al. (1983) Proc. Natl. Acad. Sci. U.S.A. 80:21-25).

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHOS promoter, a CUP1 promoter, a GALT promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*).

For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Additional exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the invention also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

Selection of the appropriate vector and promoter is well within the level of ordinary skill in the art.

A polynucleotide comprising a nucleotide sequence encoding an antibody of the present disclosure can be present in any vector, e.g., an expression vector or a cloning vector, known in the art. As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Large numbers of suitable vectors and promoters are known to those of skill in the art; many are commercially available for generating a subject recombinant vector. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia). Suitable expression vectors include, but are not limited to, viral vectors. Examples of viral vectors include, but are not limited to, viral vectors based on: vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO94/12649, WO93/03769; WO93/19191; WO94/28938; WO95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus (see, e.g., Miyoshi et al., PNAS 94:10319 23, 1997; Takahashi et al., J Virol 73:7812 7816, 1999), myeloproliferative sarcoma virus, and mammary tumor virus); and the like.

In some embodiments, the vector is a viral vector comprising a nucleic acid sequence selected from the group consisting of a retrovirus, such as Moloney murine leukemia virus, Harvey murine sarcoma virus, murine mammary tumor virus, and Rous sarcoma virus; adenovirus, adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In another embodiment, the viral vector is an adeno-associated virus (AAV) that has been manipulated to carry a polynucleotide encoding an anti-C1s antibody as disclosed herein. General methods for obtaining recombinant AAVs (rAAVs) have been disclosed. See, for example, U.S. Pat. Nos. 8,734,809, 2013/0195801 as well as the references cited therein. In some embodiments, a rAAV vector comprises one or more AAV inverted terminal repeats (ITRs) and a transgene of interest (e.g., an optimized FIX polynucleotide sequence). In certain embodiments, the methods of making rAAV involve culturing a desired host cell which contains a nucleic acid sequence encoding an AAV capsid protein or fragment thereof; a functional rep gene; a rAAV vector composed of, AAV inverted terminal repeats (ITRs) and a transgene of interest; and sufficient helper functions to permit packaging of the recombinant AAV vector into the AAV capsid proteins. Materials and methods for performing these and related procedures have been disclosed, for example, in U.S. Pat. Nos. 8,734,809, 2013/0195801, PCT/US1997/015692, PCT/US2002/033692, PCT/US2002/033630, WO2007/148971, WO00/20561, WO03/042361, and WO2007/04670.

One or more of different AAV vector sequences derived from nearly any serotype can be used in accord with the present invention. Choice of a particular AAV vector sequence will be guided by known parameters such as tropism of interest, required vector yields, etc. Generally, the AAV serotypes have genomic sequences of significant homology at the amino acid and the nucleic acid levels, provide a related set of genetic functions, produce virions which are related, and replicate and assemble similarly. For the genomic sequence of the various AAV serotypes and an overview of the genomic similarities see e.g. GenBank Accession number U89790; GenBank Accession number J01901; GenBank Accession number AF043303; GenBank Accession number AF085716; Chlorini et al. (1997, J. Vir. 71: 6823-33); Srivastava et al. (1983, J. Vir. 45:555-64); Chlorini et al. (1999, J. Vir. 73:1309-1319); Rutledge et al. (1998, J. Vir. 72:309-319); and Wu et al. (2000, J. Vir. 74: 8635-47). AAV serotypes 1, 2, 3, 4 and 5 are an illustrative source of AAV nucleotide sequences for use in the context of the present invention. AAV6, AAV7, AAV8 or AAV9 or newly developed AAV-like particles obtained by e.g. capsid shuffling techniques and AAV capsid libraries, or from newly designed, developed or evolved ITR's are also suitable for certain invention applications. See Dalkara, D et al. (2013), Sci Transl. Med. 5(189): 189ra76; Kotterman, M A Nat. Rev. Genet. (2014) 15(7):455.

In other embodiments, the vector is derived from lentivirus. In certain embodiments, the vector is a vector of a recombinant lentivirus capable of infecting non-dividing cells.

The lentiviral genome and the proviral DNA typically have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA.

However, the resulting mutant remains capable of directing the synthesis of all virion proteins. The invention provides a method of producing a recombinant lentivirus capable of infecting a non-dividing cell comprising transfecting a suitable host cell with two or more vectors carrying the packaging functions, namely gag, pol and env, as well as rev and tat. As will be disclosed herein below, vectors lacking a functional tat gene are desirable for certain applications. Thus, for example, a first vector can provide a nucleic acid encoding a viral gag and a viral pol and another vector can provide a nucleic acid encoding a viral env to produce a packaging cell. Introducing a vector providing a heterologous gene, herein identified as a transfer vector, into that packaging cell yields a producer cell which releases infectious viral particles carrying the foreign gene of interest.

According to the above-indicated configuration of vectors and foreign genes, the second vector can provide a nucleic acid encoding a viral envelope (env) gene. The env gene can be derived from nearly any suitable virus, including retroviruses. In some embodiments, the env protein is an amphotropic envelope protein which allows transduction of cells of human and other species.

Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV G), that of hepatitis viruses and of influenza also can be used.

The vector providing the viral env nucleic acid sequence is associated operably with regulatory sequences described elsewhere herein.

In certain embodiments, the vector includes a lentiviral vector in which the HIV virulence genes env, vif, vpr, vpu and nef were deleted without compromising the ability of the vector to transduce non-dividing cells.

In some embodiments, the vector includes a lentiviral vector which comprises a deletion of the U3 region of the 3' LTR. The deletion of the U3 region can be the complete deletion or a partial deletion.

In some embodiments, the lentiviral vector of the invention comprising a nucleotide sequence encoding an antibody described herein can be transfected in a cell with (a) a first nucleotide sequence comprising a gag, a pol, or gag and pol genes and (b) a second nucleotide sequence comprising a heterologous env gene; wherein the lentiviral vector lacks a functional tat gene. In other embodiments, the cell is further transfected with a fourth nucleotide sequence comprising a rev gene. In certain embodiments, the lentiviral vector lacks functional genes selected from vif, vpr, vpu, vpx and nef, or a combination thereof.

In certain embodiments, a lentiviral vector comprises one or more nucleotide sequences encoding a gag protein, a Rev-response element, a central polypurine track (cPPT), or any combination thereof.

Examples of the lentiviral vectors are disclosed in WO9931251, WO9712622, WO9817815, WO9817816, and WO9818934, which are incorporated herein by reference in their entireties.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, Calif.). Other plasmids are well-known to those of ordinary skill in the art. Additionally, plasmids can be custom designed using standard molecular biology techniques to remove and/or add specific fragments of DNA.

V. Host Cells

The present disclosure provides isolated genetically modified host cells (e.g., in vitro cells) that are genetically modified with a subject nucleic acid. In some embodiments, a subject isolated genetically modified host cell can produce a subject antibody. Such a cell is referred to as a "recombinant cell" or a "genetically modified host cell." A genetically modified host cell of the present disclosure comprises a nucleic acid comprising a nucleotide sequence encoding an antibody of the present disclosure.

Suitable host cells include eukaryotic host cells, such as a mammalian cell; an insect host cell; a yeast cell; and a prokaryotic cell, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), CVI (monkey kidney line), RAT1 cells, mouse L cells (ATCC No. CCLI.3), human embryonic kidney (HEK) cells (ATCC No. CRL1573), HLHepG2 cells, and the like. In some cases, the cells are HEK cells. In certain embodiments, the cells are HEK293 cells. In some cases, the cells are CHO cells, e.g., CHO-K1 cells (ATCC No. CCL-61), CHO-M cells, CHO-DG44 cells (ATCC No. PTA-3356), DUXB11 (Chinese Hamster Ovary line, DHFR minus), R1610 (Chinese hamster fibroblast), BALBC/3T3 (mouse fibroblast), HAK (hamster kidney line), SP2/0 (mouse myeloma), P3x63-Ag3.653 (mouse myeloma), BFA-1c1BPT (bovine endothelial cells), RAJI (human lymphocyte), PER.C6®, NS0, CAP, BHK21, and the like. In some embodiments, the host cell is a COS cell. In some embodiments, the host cell is a 293 cell. In some embodiments, the host cell is a CHO cell.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like. In some embodiments, the host cell is a *Saccharomyces*. In some embodiments, the host cell is a *Pichia*.

Suitable prokaryotic cells include, but are not limited to, any of a variety of laboratory strains of *Escherichia coli*, *Bacillus* (e.g., *B. subtilis*), *Lactobacillus* sp., and the like. See, e.g., Carrier et al. (1992) *J. Immunol.* 148:1176-1181; U.S. Pat. No. 6,447,784; and Sizemore et al. (1995) *Science* 270:299-302. Typically, the laboratory strain is one that is non-pathogenic. In some embodiments, the host cell is *Escherichia coli*. In some embodiments, the host cell is *Bacillus subtilis*.

Introduction of the isolated nucleic acid molecules of the invention into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

Host cells comprising the isolated nucleic acid molecules of the invention are grown in an appropriate growth medium. As used herein, the term "appropriate growth medium" means a medium containing nutrients required for the growth of cells. Nutrients required for cell growth can include a carbon source, a nitrogen source, essential amino acids, vitamins, minerals, and growth factors. Optionally, the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment, the medium is CDoptiCHO (Invitrogen, Carlsbad, Calif.). In another embodiment, the medium is CD17 (Invitrogen, Carlsbad, Calif.). Selection of a medium appropriate for the particular cell line used is within the level of those ordinary skilled in the art.

VI. Pharmaceutical Compositions

Compositions containing the antibodies of the present invention may contain a suitable pharmaceutically acceptable carrier. For example, they may contain excipients and/or auxiliaries that facilitate processing of the active compounds into preparations designed for delivery to the site of action.

The pharmaceutical composition can be formulated for parenteral administration (i.e. intravenous, subcutaneous, or intramuscular).

Compositions of the invention may be in a variety of forms, including, for example, liquid (e.g., injectable and infusible solutions), dispersions, suspensions, semi-solid and solid dosage forms. The preferred form depends on the mode of administration and therapeutic application.

Dosage regimens may be adjusted to provide the optimum desired response. For example, a single bolus may be administered, several divided doses may be administered over time, or the dose may be proportionally reduced or increased as indicated by the exigencies of the therapeutic situation. It is advantageous to formulate parenteral compositions in dosage unit form for ease of administration and uniformity of dosage. See, e.g., Remington's Pharmaceutical Sciences (Mack Pub. Co., Easton, Pa. 1980).

Non-limiting examples of suitable pharmaceutical carriers are also described in Remington's Pharmaceutical Sciences by E. W. Martin. Some examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents, emulsifying agents, non-aqueous vehicles, and preservatives. The preparations can also include flavoring, coloring and sweetening agents. Alternatively, the composition can be presented as a dry product for constitution with water or another suitable vehicle.

For buccal administration, the composition may take the form of tablets or lozenges according to conventional protocols.

For administration by inhalation, the compounds for use according to the present invention are conveniently delivered in the form of a nebulized aerosol with or without excipients or in the form of an aerosol spray from a pressurized pack or nebulizer, with optionally a propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can also be formulated for rectal administration as a suppository or retention enema, e.g., containing conventional suppository bases such as cocoa butter or other glycerides.

In one embodiment, a pharmaceutical composition comprises a antibody, e.g., an anti-Factor B antibody, bispecific antibody, or multispecific antibody, a polynucleotide encoding the antibody, a vector comprising the polynucleotide, or a host cell comprising the vector, and a pharmaceutically acceptable carrier.

Having now described the present invention in detail, the same will be more clearly understood by reference to the following examples, which are included herewith for purposes of illustration only and are not intended to be limiting of the invention.

EXAMPLES

Example 1

Production of Anti-Factor B Antibodies

Anti-human Complement Factor B (fBb) monoclonal antibodies were produced as follows: Immunization of NZBW mice with purified fBb protein generated a hybridoma library that was screened for binding to target using techniques known to those skilled in the art. Flow cytometry was used to generate single cell clones, and supernatants from these individual clones were screened for preferential binding to fBb by direct enzyme-linked immunosorbent assay (ELISA). Clones with specific binding to fBb were expanded in culture, and monoclonal antibodies were purified from hybridoma supernatants. Purified mAbs were further screened for inhibition of alternative pathway (AP) activity using the Complement System Alternative Pathway WIESLAB kit (Euro Diagnostica, Sweden). From these results, a novel antibody that binds to fBb was identified. The antibody herein was designated as anti-Factor B Ab.

Example 2

Binding Affinity Binding of Anti-Factor B Ab to Human Factor B

The relative $EC_{50}$ values for anti-Factor B Ab were determined by ELISA. Unlabeled purified human Factor Bb was coated onto a high binding ELISA plate, and incubated with increasing amounts of purified mAbs (3-fold serial dilutions starting at 10 µg/mL). Horse radish peroxidase (HRP)-conjugated goat anti-mouse secondary antibody (Southern Biotech) was used for detection, and reacted with 3,3',5,5'-Tetramethylbenzidine (TMB) 1-Step Ultra TMB-ELISA Substrate Solution (Thermo Scientific). Reactions were stopped with an equal volume of 1N sulfuric acid; and absorbance at $OD_{450}$ nm was measured. The $EC_{50}$ for each monoclonal was calculated using PRISM software. Anti-Factor B Ab was found to bind to both full length human Complement Factor B and its active enzymatic form, Factor Bb, with similar affinity.

Example 3

Anti-Factor B Ab Blocks Factor H Dissociation of C3bBb Complex

Pre-incubation of anti-Factor B Ab in either human or cynomolgus monkey serum results in a concentration-dependent attenuation of the alternative pathway of complement (AP), demonstrated in vitro using an AP ELISA kit or in rabbit red blood cell hemolysis experiments designed to specifically activate the AP.

Using the Octet System (Pall ForteBio), the effect of the anti-Factor B antibody on the dissociation rate of the C3bBb complex by Factor H (FH) was examined. Briefly, biotinylated properdin was prepared and bound to Octet probes coated with Streptavidin. Afterwards, the bound properdin probes were incubated in C3bBb complex containing solution comprising 10 mM HEPES, 150 mM NaCl, 2 mM $MgCl_2$, 0.05% Tween-20. The solution was prepared by mixing an antibody (anti-Factor B Ab, anti-Factor B F(ab')2, Quidel α-fB, anti-Factor B Fab, C3bBb, C3b+fB, or C3b alone) at a concentration of 50 µg/mL. As the C3 convertase binds the properdin probe, the association was measured. See FIG. 1. After 600 seconds of incubation, the probe was transferred to a solution containing only buffer to measure the dissociation of the C3bBb complex from the properdin bound probe. At 780 seconds after the commencement of the experiment, a dissociation solution comprising 50 µg/mL Factor H in Assay Buffer was added. As shown in FIG. 1A, anti-Factor B Ab remained most strongly bound to the C3bBb complex. This demonstrates that anti-Factor B Ab prevents Factor H, the primary fluid phase inhibitor of the AP C3 convertase in the C3bBb complex, from binding to and disrupting the C3bBb complex.

Example 4

Anti-Factor B Ab Blocks CD55 Dissociation of C3bBb Complex

Using the same Octet System described in Example 3 above, the effect of the anti-Factor B antibody on the dissociation rate of the C3bBb complex by CD55 was examined. Briefly, biotinylated properdin was prepared and bound to Octet probes coated with Streptavidin. Afterwards, the bound properdin probes were incubated in C3bBb complex containing solution comprising 10 mM HEPES, 150 mM NaCl, 2 mM $MgCl_2$, 0.05% Tween-20. The solution was prepared by mixing an antibody (anti-Factor B Ab, anti-Factor B F(ab')2, Quidel α-fB, anti-Factor B Fab, C3bBb, C3b+fB, or C3b alone) at a concentration of 50 µg/mL. As the C3 convertase binds the properdin probe, the association was measured. See FIG. 2. After 600 seconds of incubation, the probe was transferred to a solution containing only buffer to measure the dissociation of the C3bBb complex from the properdin bound probe. At 780 seconds after the commencement of the experiment, a dissociation solution comprising 50 µg/mL CD55 in Assay Buffer was added. As shown in FIG. 1B, anti-Factor B Ab remained most strongly bound to the C3bBb complex, preventing CD55 from binding to and disrupting the dissociation of the C3bBb complex. These data demonstrate that anti-Factor B Ab prevents the binding of DAF/CD55 to the C3 AP convertase, a membrane bound inhibitory regulator of the complement cascades.

Example 5

Anti-Factor B Ab Induces C3 Cleavage in Serum

Normal human serum was tested to determine if M4 induces cleavage of C3 in serum. After initial incubation with a CAP dilution buffer, M4, M4 Fab, or Quidel α-fB were added to the samples. As negative control, 10% NHS in CAP dilution buffer alone or Cap dilution buffer with a mIgG2a antibody was added to serum. At 10 minutes, 20 minutes, or 30 minutes after addition of an antibody to a serum sample, aliquots of serum were taken and added to sample buffer (comprising a reducing agent). Lysates extracted from the serum were analyzed via Western blot. Lysates were run on 4-12% NuPAGE Gel (MES Buffer), reduced. After transfer to a membrane, the membrane was incubated with a polyclonal rabbit a human C3 primary antibody at a dilution of 1:1000 and detected using a Licor anti-rabbit IgG secondary antibody at a dilution of 1:5000.

Figure 2:
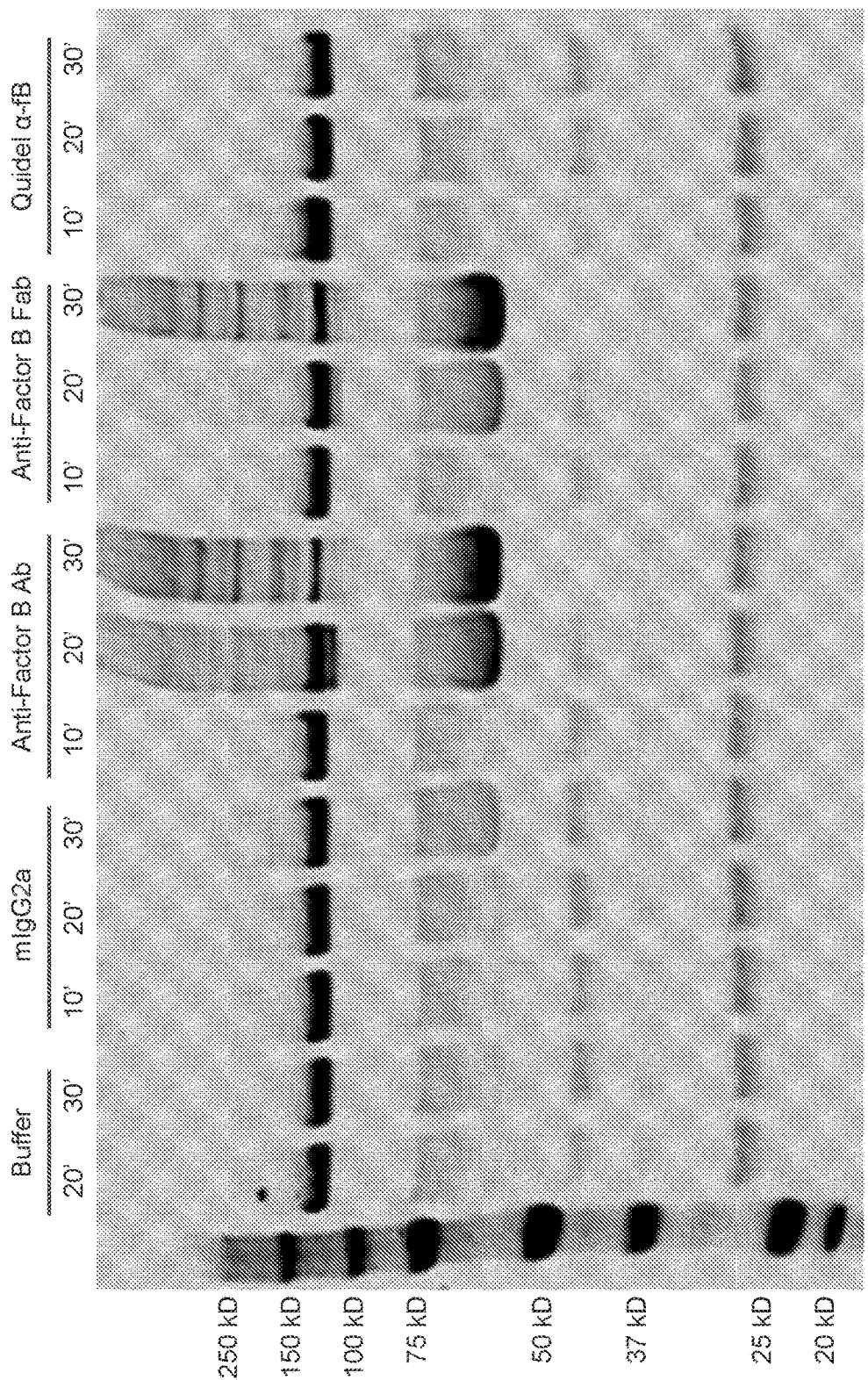
FIG. 2 is an image of a Western blot, detecting C3 cleavage in serum samples treated with a Factor B antibody. Human C3 is normally detected at about 140 kD. Aliquots were analyzed after 10 minutes, 20 minutes, or 30 minutes of incubation with buffer comprising a Factor B antibody (anti-Factor B Ab, anti-Factor B-Fab, or Quidel α-fB).

Normal C3 is detected at about 140 kD. As shown in FIG. 2, anti-Factor B Ab and anti-Factor B Fab (but not serum incubated with buffer alone, mIgG2a, or Quidel α-fB) induced C3 cleavage in a time dependent manner. There was also a time dependent reduction of normal C3 expression with treatment of anti-Factor B Ab and anti-Factor B Fab. A cleaved C3 is detected at about 65 kD in samples incubated with anti-Factor B Ab for 20 minutes and 30 minutes, demonstrating cleavage of C3.

Example 6

Anti-Factor B Ab Blocks Both Factor H and CD55 DAF Activity in Solution

Next, normal human serum was tested to determine if anti-Factor B Ab blocks both Factor H and DAF/CD55 activity in solution. After initial incubation with C3, Factor B, anti-Factor B Ab, Factor H, and/or DAF/CD55, Factor D was added to the samples, and incubated at 37° C. for 45 mins. After 45 minutes, aliquots of serum were taken and added to sample buffer (comprising a reducing agent). Lysates extracted from the serum were separated on a gel and analyzed using a Coomassie stain. As shown in FIG. 3, while treatment only of Factor H or DAF/CD55 maintains normal C3 expression, treatment of anti-Factor B Ab with Factor H or DAF/CD55 causes cleavage of C3. See double band at about 140 kD in lanes 7 and 9 compared to single band in lanes 6 and 8. Thus, anti-Factor B Ab blocks both Factor H and DAF/CD55 activity in solution.

Example 7

Chimeric Anti-Factor B Ab

Variable domains for hybridoma clones anti-Factor B Ab were synthesized along with additional flanking sequences needed for cloning. The variable domains were cloned into expression vectors that generated a chimeric antibody composed of mouse variable regions and human IgG4 constant/Fc regions. The constructs were transfected into HEK293 cells and purified from culture supernatants using Protein A Sepharose. The chimeric antibody containing the variable region of anti-Factor B Ab that was grafted onto the constant region of a human IgG4 antibody is referred to as chimeric anti-Factor B Ab.

Example 8

In Vivo Assay Using Chimeric Anti-Factor B Ab

In vivo experiments were performed to assess the pharmacokinetics and pharmacodynamics of chimeric anti-Factor B Ab in cynomolgus monkeys. Briefly, cynomolgus monkeys were administered 30 mg/kg of chimeric anti-Factor B Ab intravenously. Plasma and serum were collected at various time points up to 30 days. As shown in FIG. 4, analyses of serum and plasma samples taken at specific time points throughout the course of the PK/PD study revealed that intravenous administration of chimeric anti-Factor B Ab lead to the loss of detectable serum AP activity in the dosed animals.

Serum classical pathway activity was also found to be significantly attenuated. Western blot analyses of these samples showed a drop in C3, a finding confirmed using an in-house ELISA constructed to measure cynomolgus monkey plasma C3 concentrations.

Together with the data from the in vivo study, these results led to the hypothesis that anti-Factor B Ab and chimeric anti-Factor B Ab bind to and stabilize both the fluid and solid phase AP C3 convertase, preventing its degradation and resulting in the consumption of C3 and the loss of serum complement activity.

Example 9

Therapeutic Use of a Humanized Antibody of Anti-Factor B Ab

A fully humanized version of anti-Factor B Ab or chimeric anti-Factor B Ab that binds to and prevents the inhibition of the AP C3 convertase is used to therapeutically target and induce complement activity on the surface of a cell of a patient with an impaired innate immune system.

Example 10

Therapeutic Use of a Bispecific Antibody of Anti-Factor B Ab

A bispecific antibody is constructed with humanized anti-Factor B Ab and the variable region (or for example the F(ab), or F(ab')2 region) of a second antibody that binds to a membrane bound protein on a cell of interest, using the second antibody of the bispecific as a homing mechanism. For instance, a bispecific antibody consisting of humanized anti-Factor B Ab on one end and a variable region directed against CD20 on the other end, could be used to specifically target B cells (either in the case of lymphomas or autoimmune diseases). Similarly, a bispecific antibody comprising humanized anti-Factor B Ab, or a fragment thereof, and a variable region targeting the voltage gated potassium channel Kv1.3 (which is upregulated on the surface of autoantigen specific T effector cells in patients with autoimmune diseases such as multiple sclerosis and type 1 diabetes) could be used to activate the complement cascade specifically on the surface of autoimmune lymphocytes while preserving non-self-reacting lymphocytes. Thus, using the variable regions of humanized anti-Factor B Ab and a homing antibody in a bispecific manner provides a platform for focusing complement activity on the surface of any cell type of interest.

Example 11

Alternative Complement Pathway Inhibition Does Not Prevent Whole Blood Killing of Antibody-Coated N. meningitidis or S. pneumoniae Background: The complement cascade, responsible for the detection and clearance of pathogens, is activated by the classical (CP), lectin (LP) or alternative (AP) pathways, each of which can be independently activated by pathway-specific pattern recognition receptors. However, aberrant complement activation is observed in numerous diseases. While therapeutic complement inhibition at the level of C5 has proven to be a successful approach for treating various diseases, it is associated with an increased risk of infection, in particular, invasive meningococcal disease, even when vaccinating prophylactically. Targeting pathway-specific components provides the theoretical advantage of selectively inhibiting the pathway that triggers disease pathogenesis, while leaving the other pathways intact for immune surveillance.

Aim: This experiment is to find out whether an anti-factor Bb antibody exhibits a potential increased infection risk. We performed in vitro bactericidal (complement-mediated) and whole blood killing assays (complement- and immune cell-mediated) to assess the relative contribution of the AP in killing N. meningitidis and S. pneumoniae.

Methods: Experiments were performed using S. pneumoniae strain TIGR4 and group C N. meningitidis strain 4243. Flow cytometry was used to measure deposition of C3 and C4; pathway specific inhibitors were used to determine the relative contribution of the different pathways in depositing opsonizing complement fragments on bacteria. Bactericidal experiments in normal human plasma and whole blood killing assays containing both intact complement and phagocytes, were performed in the presence of an anti-factor Bb antibody. Experiments were performed in the presence or absence of capsular antibody to mimic vaccinated and non-vaccinated states, respectively.

Results: Inhibiting the CP alone using saturating concentrations of an anti-C1s antibody prevented C4 deposition and killing of N. meningitidis in both normal human plasma and whole blood. However, in whole blood killing assays that contained specific anti-meningococcal antibodies, simultaneous inhibition of both the CP and AP was required to prevent killing of antibody-coated N. meningitidis. For antibody-coated S. pneumoniae, anti-factor Bb antibody alone completely blocked C3 deposition. As expected, killing of S. pneumoniae was observed only in whole blood in the presence of phagocytes; blocking the AP did not impair killing of pneumococci in the presence of specific antibody (>90% killing at 3 h).

Conclusions: The data presented here suggest that antibody-coated N. meningitidis can activate the AP of complement, and that inhibition of the pathway would not significantly affect N. meningitidis killing in the presence of anti-N. meningitidis antibodies as membrane attack complex mediated killing could still occur via the unblocked pathway. Antibody-mediated killing of S. pneumoniae, which requires phagocytes, also proceeded in an unimpeded manner when the AP was blocked. These data suggest that vaccination against N. meningitidis and S. pneumoniae is critical and likely to be effective when administering a therapeutic AP inhibitor.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All publications, patents, and patent applications disclosed herein are incorporated by reference to the same extent as if each individual publication, patent or patent application was specifically and individually indicated to be incorporated by reference.

What is claimed is:

1. A bispecific antibody comprising (i) an antigen binding domain that specifically binds Factor B and Factor Bb (an anti-Factor B binding domain) and inhibits dissociation of a C3bBb complex and (ii) a second antigen binding domain that is tissue or cell specific, wherein the anti-Factor B binding domain comprises a complementarity determining region-1 (CDR1), a CDR2, and a CDR3 of a heavy chain variable region (VH) comprising the amino acid sequence of SEQ ID NO: 7 and a CDR1, CDR2, and a CDR3 of a light chain variable region (VL) comprising the amino acid sequence of SEQ ID NO: 8.

2. The bispecific antibody of claim 1, wherein the anti-Factor B binding domain has one or more properties selected from the group consisting of: (i) specifically binds to a C3bBb complex, (ii) reduces, inhibits, or prevents degradation of a C3bBb complex, (iii) induces a complement activity, (iv) induces C3 cleavage in serum, (v) reduces serum concentration of C3, (vi) induces accumulation of C3b on the surface of the cell (vii) induces membrane attack complex deposition on the cell surface, and (viii) any combination thereof.

3. The bispecific antibody of claim 1, wherein the anti-Factor B binding domain reduces or blocks CD55-mediated dissociation of the C3bBb complex.

4. The bispecific antibody of claim 1, wherein the anti-Factor B binding domain reduces or blocks Factor-H mediated dissociation of the C3bBb complex.

5. A polynucleotide comprising a nucleic acid encoding the bispecific antibody of claim 1.

6. A method of inducing a complement activity on a surface of a cell in a subject, comprising contacting the cell with an effective amount of the bispecific antibody of claim 1.

7. A multispecific antibody comprising (i) an antigen binding domain that specifically binds Factor B and Factor Bb (an anti-Factor B binding domain) and inhibits dissociation of a C3bBb complex, (ii) a second antigen binding domain that is tissue or cell specific, and (iii) a third antigen binding domain, wherein the anti-Factor B binding domain comprises a complementarity determining region-1 (CDR1), a CDR2, and a CDR3 of a heavy chain variable region (VH) comprising the amino acid sequence of SEQ ID NO: 7 and a CDR1, CDR2, and a CDR3 of a light chain variable region (VL) comprising the amino acid sequence of SEQ ID NO: 8.

8. A polynucleotide comprising a nucleic acid encoding the multispecific antibody of claim 7.

9. A method of inducing a complement activity on a surface of a cell in a subject, comprising contacting the cell with an effective amount of the multispecific antibody of claim 7.

10. A method of inducing a complement activity on a surface of a cell in a subject, comprising contacting the cell with an effective amount of an antibody that specifically binds Factor B and Factor Bb (anti-Factor B antibody), wherein the anti-Factor B antibody comprises a complementarity determining region-1 (CDR1), a CDR2, and a CDR3 of a heavy chain variable region (VH) comprising the amino acid sequence of SEQ ID NO: 7 and a CDR1, CDR2, and a CDR3 of a light chain variable region (VL) comprising the amino acid sequence of SEQ ID NO: 8, and wherein the anti-Factor B antibody inhibits dissociation of a C3bBb complex.

11. The method of claim 10, wherein the anti-Factor B antibody has one or more properties selected from the group consisting of: (i) specifically binds to a C3bBb complex, (ii) reduces, inhibits, or prevents degradation of a C3bBb complex, (iii) induces C3 cleavage in serum, (iv) reduces serum concentration of C3, (v) induces accumulation of C3b on the surface of the cell (vi) induces the loss of serum complement activity, (vii) induces membrane attack deposition on the cell surface, and (viii) any combination thereof.

12. The method of claim 10, wherein the subject has a disease or condition to be treated.

13. The method of claim 12, wherein the disease or condition comprises a cancer, an infection, or an autoimmune disease.

* * * * *